United States Patent
Wexler-Cohen et al.

(10) Patent No.: US 12,156,900 B2
(45) Date of Patent: Dec. 3, 2024

(54) VEGFR-FC FUSION PROTEIN FORMULATIONS

(71) Applicant: Amgen Inc., Thousand Oaks, CA (US)

(72) Inventors: Yael Wexler-Cohen, Thousand Oaks, CA (US); William J. Callahan, Thousand Oaks, CA (US); Robert Matthew Fesinmeyer, Newbury Park, CA (US); Rahul Rajan Kaushik, Newbury Park, CA (US); Sai Chakradhar Padala, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 153 days.

(21) Appl. No.: 16/764,463

(22) PCT Filed: Nov. 16, 2018

(86) PCT No.: PCT/US2018/061644
§ 371 (c)(1),
(2) Date: May 15, 2020

(87) PCT Pub. No.: WO2019/099921
PCT Pub. Date: May 23, 2019

(65) Prior Publication Data
US 2020/0338164 A1    Oct. 29, 2020

Related U.S. Application Data

(60) Provisional application No. 62/618,904, filed on Jan. 18, 2018, provisional application No. 62/587,733, filed on Nov. 17, 2017.

(51) Int. Cl.
| | |
|---|---|
| *A61K 38/18* | (2006.01) |
| *A61K 9/00* | (2006.01) |
| *A61K 47/02* | (2006.01) |
| *A61K 47/14* | (2017.01) |
| *A61K 47/18* | (2017.01) |
| *A61K 47/26* | (2006.01) |
| *A61K 47/34* | (2017.01) |

(52) U.S. Cl.
CPC ........ *A61K 38/1866* (2013.01); *A61K 9/0048* (2013.01); *A61K 47/02* (2013.01); *A61K 47/14* (2013.01); *A61K 47/183* (2013.01); *A61K 47/26* (2013.01); *A61K 47/34* (2013.01)

(58) Field of Classification Search
None
See application file for complete search history.

(56) References Cited

U.S. PATENT DOCUMENTS

| | | |
|---|---|---|
| 7,531,173 B2 | 5/2009 | Wiegand et al. |
| 7,608,261 B2 | 10/2009 | Furfine et al. |
| 7,648,702 B2 | 1/2010 | Gombotz et al. |
| 7,807,164 B2 | 10/2010 | Furfine et al. |
| 8,092,803 B2 | 1/2012 | Furfine et al. |
| 8,110,546 B2 | 2/2012 | Dix et al. |
| 8,404,638 B2 | 3/2013 | Dix et al. |
| 8,481,046 B2 | 7/2013 | Furfine et al. |
| 8,710,004 B2 | 4/2014 | Dix et al. |
| 8,802,107 B2 | 8/2014 | Furfine et al. |
| 8,921,316 B2 | 12/2014 | Dix et al. |
| 9,340,594 B2 | 5/2016 | Furfine et al. |
| 9,416,167 B2 | 8/2016 | Dix et al. |
| 9,511,140 B2 | 12/2016 | Dix et al. |
| 9,580,489 B2 | 2/2017 | Furfine et al. |
| 9,636,400 B2 | 5/2017 | Dix et al. |
| 9,914,763 B2 | 3/2018 | Furfine et al. |
| 9,982,032 B2 | 5/2018 | Park et al. |
| 10,307,483 B2 | 6/2019 | Goss et al. |
| 10,400,025 B2 | 9/2019 | Furfine et al. |
| 10,464,992 B2 | 11/2019 | Furfine et al. |
| 10,576,128 B2 | 3/2020 | Sigl |
| 10,646,546 B2 | 5/2020 | Im |
| 11,359,026 B2 | 6/2022 | Morichika |
| 11,667,702 B2 * | 6/2023 | Liu ..................... A61K 9/0019 424/134.1 |
| 11,692,027 B2 | 7/2023 | Kraft |
| 2004/0197324 A1 | 10/2004 | Liu et al. |
| 2010/0272719 A1 | 10/2010 | Yu |
| 2012/0028877 A1 | 2/2012 | Gokarn et al. |
| 2013/0323242 A1 | 12/2013 | Everett et al. |
| 2014/0356358 A1 | 12/2014 | Sun |
| 2016/0376342 A1 | 12/2016 | Park et al. |

(Continued)

FOREIGN PATENT DOCUMENTS

| | | |
|---|---|---|
| CN | 103212075 B | 6/2017 |
| CN | 103816115 B | 6/2017 |

(Continued)

OTHER PUBLICATIONS

Rasouli et al. ("Effect of sucrose and trehalose on stability, kinetic properties and thermal aggregation of firefly luciferase" Appl Biochem Biotechnol (2011) 165:572-582).*

(Continued)

*Primary Examiner* — Julie Ha
*Assistant Examiner* — Tara L Martinez
(74) *Attorney, Agent, or Firm* — Margareta K. Sorenson

(57) ABSTRACT

Protein formulations and methods of making and using such formulations are provided herein. The formulation can be an ophthalmic formulation, such as for intravitreal administration. In some embodiments, the formulation comprises a VEGFR-Fc fusion protein, such as aflibercept.

12 Claims, 4 Drawing Sheets

Specification includes a Sequence Listing.

(56) References Cited

U.S. PATENT DOCUMENTS

| | | |
|---|---|---|
| 2017/0181978 A1 | 6/2017 | Chen et al. |
| 2017/0305996 A1 | 10/2017 | Kim |
| 2018/0236070 A1 | 8/2018 | Ioffe et al. |
| 2018/0289623 A1 | 10/2018 | Chen et al. |
| 2019/0030123 A1 | 1/2019 | Sigl |
| 2019/0160145 A1 | 5/2019 | Im et al. |
| 2019/0276528 A1 | 9/2019 | Liu et al. |
| 2019/0298801 A1 | 10/2019 | Kerwin et al. |
| 2019/0343918 A1 | 11/2019 | Graham et al. |
| 2020/0017572 A1 | 1/2020 | Furfine et al. |
| 2020/0022917 A1 | 1/2020 | Brudnicki |
| 2020/0031917 A1 | 1/2020 | Kraft et al. |
| 2020/0215079 A1 | 7/2020 | Yang et al. |
| 2020/0246423 A1 | 8/2020 | Liu et al. |
| 2020/0255496 A1 | 8/2020 | Wexler-Cohen et al. |
| 2020/0338164 A1 | 10/2020 | Wexler-Cohen et al. |
| 2020/0390693 A1 | 12/2020 | Kim et al. |
| 2021/0170029 A1 | 6/2021 | Gillespie |

FOREIGN PATENT DOCUMENTS

| | | |
|---|---|---|
| EP | 3199179 B1 | 12/2021 |
| KR | 101685532 | 12/2016 |
| WO | 2013181495 A2 | 12/2013 |
| WO | 2014039682 | 3/2014 |
| WO | 2014078627 A1 | 5/2014 |
| WO | 2016208989 | 12/2016 |
| WO | 2017066554 | 4/2017 |
| WO | 2017106716 A1 | 6/2017 |
| WO | 2017129685 | 8/2017 |
| WO | 2017168296 | 10/2017 |
| WO | 2018094316 A1 | 5/2018 |
| WO | 2018116198 A1 | 6/2018 |
| WO | WO2018199408 * | 11/2018 |
| WO | 2019020777 A1 | 1/2019 |
| WO | 2019057110 A1 | 3/2019 |
| WO | 2019099965 A1 | 5/2019 |
| WO | 2019124946 A1 | 6/2019 |
| WO | 2020055123 A1 | 3/2020 |
| WO | 2020087003 A1 | 4/2020 |
| WO | 2020165132 A1 | 8/2020 |
| WO | 2021028669 A1 | 2/2021 |
| WO | 2021050687 A1 | 3/2021 |

OTHER PUBLICATIONS

Bahrenburg et al. (Biotechnology Journal, vol. 10 (issue 4), Apr. 2015).*
International Search Report for PCT/US2019/058144, mailed Feb. 17, 2020, 7 pages.
Written Opinion for PCT/US2019/058144, mailed Feb. 17, 2020, 6 pages.
International Search Report for PCT/US2018/051311, mailed Dec. 7, 2018, 6 pages.
Written Opinion for PCT/US2018/051311, mailed Dec. 7, 2018, 5 pages.
International Search Report for PCT/US2018/061644, mailed May 15, 2019, 7 pages.
Written Opinion for PCT/US2018/061644, mailed May 15, 2019, 8 pages.
Alibercept Product Information, Attachment 1: Product Information for AusPAR Zaltrap/Lidaveg/Aflitiv; Aflibercept; Sanofi-Aventis Australia Pty Ltd; PM-2011-04301-3-4 Date of Finalisation Jul. 29, 2013. (2013).
Liu et al., "A novel engineered VEGR blocker with an excellent pharmacokinetic profile and robust anti-tumor activity," BMC Cancer, vol. 15, No. 25 (2015).
Berger et al., "Fusion protein technologies for biopharmaceuticals: Applications and challenges," mAbs, vol. 7(3), pp. 456-460 (2015).
Czajkowsky et al., "Fc-fusion proteins: new developments and future perspectives," EMBO Molecular Medicine, vol. 4(10), pp. 1015-1028 (2012).
Gokarn et al., "Self-Buffering Antibody Formulations", Journal of Pharmaceutical Sciences, vol. 97 (8), pp. 3051-3066 (Aug. 2008).
Kheddo et al., "The effect of arginine glutamate on the stability of monoclonal antibodies in solution," International Journal of Pharmaceutics, vol. 473, pp. 126-133 (2014).
Maggio, "Use of excipients to control aggregation in peptide and protein formulations," J. Excipients and Food Chem., vol. 1(2), pp. 40-49 (2010).
Mansour, "Regression of Inflamed Pterygia by Frequent High-Dose Intralesional Ziv-Aflibercept," Cornea, vol. 36(8), pp. 1002-1005 (2017).

* cited by examiner

```
                         SEQUENCE LISTING

<160> NUMBER OF SEQ ID NOS: 2

<210> SEQ ID NO 1
<211> LENGTH: 431
<212> TYPE: PRT
<213> ORGANISM: Artificial Sequence
<220> FEATURE:
<223> OTHER INFORMATION: Fusion Protein

<400> SEQUENCE: 1

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
```

-continued

```
                325                 330                 335
Pro Pro Ser Arg Asp Glu Leu Thr Lys Asn Gln Val Ser Leu Thr Cys
            340                 345                 350
Leu Val Lys Gly Phe Tyr Pro Ser Asp Ile Ala Val Glu Trp Glu Ser
            355                 360                 365
Asn Gly Gln Pro Glu Asn Asn Tyr Lys Thr Thr Pro Pro Val Leu Asp
            370                 375                 380
Ser Asp Gly Ser Phe Phe Leu Tyr Ser Lys Leu Thr Val Asp Lys Ser
385                 390                 395                 400
Arg Trp Gln Gln Gly Asn Val Phe Ser Cys Ser Val Met His Glu Ala
                405                 410                 415
Leu His Asn His Tyr Thr Gln Lys Ser Leu Ser Leu Ser Pro Gly
            420                 425                 430

<210> SEQ ID NO 2
<211> LENGTH: 432
<212> TYPE: PRT
<213> ORGANISM: Artificial Sequence
<220> FEATURE:
<223> OTHER INFORMATION: Fusion Protein

<400> SEQUENCE: 2

Ser Asp Thr Gly Arg Pro Phe Val Glu Met Tyr Ser Glu Ile Pro Glu
1               5                   10                  15
Ile Ile His Met Thr Glu Gly Arg Glu Leu Val Ile Pro Cys Arg Val
                20                  25                  30
Thr Ser Pro Asn Ile Thr Val Thr Leu Lys Lys Phe Pro Leu Asp Thr
            35                  40                  45
Leu Ile Pro Asp Gly Lys Arg Ile Ile Trp Asp Ser Arg Lys Gly Phe
        50                  55                  60
Ile Ile Ser Asn Ala Thr Tyr Lys Glu Ile Gly Leu Leu Thr Cys Glu
65                  70                  75                  80
Ala Thr Val Asn Gly His Leu Tyr Lys Thr Asn Tyr Leu Thr His Arg
                85                  90                  95
Gln Thr Asn Thr Ile Ile Asp Val Val Leu Ser Pro Ser His Gly Ile
                100                 105                 110
Glu Leu Ser Val Gly Glu Lys Leu Val Leu Asn Cys Thr Ala Arg Thr
            115                 120                 125
Glu Leu Asn Val Gly Ile Asp Phe Asn Trp Glu Tyr Pro Ser Ser Lys
        130                 135                 140
His Gln His Lys Lys Leu Val Asn Arg Asp Leu Lys Thr Gln Ser Gly
145                 150                 155                 160
Ser Glu Met Lys Lys Phe Leu Ser Thr Leu Thr Ile Asp Gly Val Thr
                165                 170                 175
Arg Ser Asp Gln Gly Leu Tyr Thr Cys Ala Ala Ser Ser Gly Leu Met
                180                 185                 190
Thr Lys Lys Asn Ser Thr Phe Val Arg Val His Glu Lys Asp Lys Thr
            195                 200                 205
His Thr Cys Pro Pro Cys Pro Ala Pro Glu Leu Leu Gly Gly Pro Ser
        210                 215                 220
Val Phe Leu Phe Pro Pro Lys Pro Lys Asp Thr Leu Met Ile Ser Arg
225                 230                 235                 240
Thr Pro Glu Val Thr Cys Val Val Val Asp Val Ser His Glu Asp Pro
                245                 250                 255
Glu Val Lys Phe Asn Trp Tyr Val Asp Gly Val Glu Val His Asn Ala
```

```
                260                265                270
Lys Thr Lys Pro Arg Glu Glu Gln Tyr Asn Ser Thr Tyr Arg Val Val
        275                280                285

Ser Val Leu Thr Val Leu His Gln Asp Trp Leu Asn Gly Lys Glu Tyr
        290                295                300

Lys Cys Lys Val Ser Asn Lys Ala Leu Pro Ala Pro Ile Glu Lys Thr
305                310                315                320

Ile Ser Lys Ala Lys Gly Gln Pro Arg Glu Pro Gln Val Tyr Thr Leu
                325                330                335

Pro Pro Ser Arg Asp Glu Leu Thr Lys Asn Gln Val Ser Leu Thr Cys
                340                345                350

Leu Val Lys Gly Phe Tyr Pro Ser Asp Ile Ala Val Glu Trp Glu Ser
        355                360                365

Asn Gly Gln Pro Glu Asn Asn Tyr Lys Thr Thr Pro Pro Val Leu Asp
        370                375                380

Ser Asp Gly Ser Phe Phe Leu Tyr Ser Lys Leu Thr Val Asp Lys Ser
385                390                395                400

Arg Trp Gln Gln Gly Asn Val Phe Ser Cys Ser Val Met His Glu Ala
                405                410                415

Leu His Asn His Tyr Thr Gln Lys Ser Leu Ser Leu Ser Pro Gly Lys
                420                425                430
```

VEGFR-FC FUSION PROTEIN FORMULATIONS

RELATED APPLICATIONS

This application is a U.S. national stage filing under 35 U.S.C. § 371 of PCT Application Number PCT/US18/61644, filed on Nov. 16, 2018, which claims the benefit of U.S. Provisional Application No. 62/587,733, filed on Nov. 17, 2017, and U.S. Provisional Application No. 62/618,904, filed on Jan. 18, 2018, each of which is hereby incorporated by reference in its entirety.

SEQUENCE LISTING

The present application is being filed along with a Sequence Listing in electronic format. The Sequence Listing is provided as a file entitled A-2208-WO-PCT_SeqList_ST25.txt, created Nov. 15, 2018, which is 7.78 kb in size. The information in the electronic format of the Sequence Listing is incorporated herein by reference in its entirety.

FIELD OF THE INVENTION

The instant disclosure relates to VEGFR-Fc fusion protein formulations and methods for making and using such formulations, such as a formulation without a buffering agent or a formulation with a buffering agent in which the formulation has a pH outside the buffering capacity of the buffering agent.

BACKGROUND

Vascular endothelial growth factor (VEGF), also referred to as VEGF-A, is a signaling protein that promotes the growth of new blood vessels and binds to VEGFR-1 and VEGFR-2. VEGF has been shown to be upregulated in many tumors and has a role in angiogenesis. VEGF has also been shown to have a role in intraocular neovascularization, such as choroidal neovascularization (CNV), which is a significant aspect of wet age related macular degeneration (AMD).

VEGF inhibitors, such as anti-VEGF antibodies and fragments and decoy receptors or chimeric receptors, have been developed as therapeutics for the treatment of various conditions, such as cancer and ocular disorders. For example, an anti-VEGF antibody and an anti-VEGF Fab are both commercially available as bevacizumab and ranibizumab, respectively. Also, commercially available is aflibercept, a VEGFR-Fc fusion protein or "VEGF-trap."

Aflibercept is a fusion protein composed of an IgG1 Fc domain fused to the Ig domain 2 of VEGFR-1 and Ig domain 3 of VEGFR-2. Aflibercept is marketed as Eylea® (Regeneron, Tarrytown, N.Y.) for the treatment of various ocular conditions, including wet type AMD, and is formulated for intravitreal administration. The fusion protein is also marketed as Zaltrap® (ziv-aflibercept) (Regeneron, Tarrytown, N.Y.) for the treatment of certain types of cancer and is formulated for intravenous administration.

Ophthalmic formulations, and in particular intravitreal administration, can have additional safety concerns as compared to other administration routes, and thus, have more specific requirements. For example, impact to a subject due to inflammation or other adverse reactions can be severe, and thus, more specific requirements may be required. For example, a formulation for intravitreal administration may require a narrower range of permissible osmolarity. A formulation for intravitreal administration may require a lower threshold of permissible particulation, e.g., USP <789> versus USP <788>. It is also advantageous to have a formulation that provides increased stability.

The present disclosure provides formulations that meets the need for new protein formulations, e.g., VEGFR-Fc fusion formulations or intravitreal formulations that are stable, have less aggregation, or have related advantages.

SUMMARY

Provided herein are protein formulations and methods for making and using such formulations. In some embodiments, the formulation is suitable for intravitreal administration. In some embodiments, the protein is a VEGFR-Fc fusion protein. In some embodiments, the protein formulation is a buffer free formulation. In one embodiment, the formulation comprises a buffering agent and has a pH outside the buffering capacity of the buffering agent. In one embodiment, the formulation comprises no buffering agent.

In one embodiment, the formulation comprises a fusion protein comprising a domain of a vascular endothelial growth factor (VEGF) receptor and an Fc domain, a stabilizer, and optionally, a surfactant and/or a tonicity agent. Accordingly, in some embodiments, the formulation does not comprise a buffering agent, or comprises a residual amount of buffering agent such that the residual amount lacks buffering capacity in the formulation. The formulation can have a pH between 4.0 and 8.5. In some embodiments, the formulation can have a pH between 5.0 and 7.0, or a pH that is about 5.0, about 5.2, about 5.5, about 5.8, about 6.0, about 6.2, about 6.3, about 6.4, about 6.5, or about 6.8. In some embodiments, the pH is 5.0±0.3, 5.2±0.3, 5.5±0.3, 5.8±0.3, 6.0±0.3, 6.1±0.3, 6.2±0.3, 6.3±0.3, 6.4±0.3, 6.5±0.3 or 6.8±0.3.

In another embodiment, the formulation comprises a fusion protein comprising a domain of a vascular endothelial growth factor (VEGF) receptor and an Fc domain, a stabilizer, a buffering agent, and optionally, a surfactant and/or a tonicity agent, wherein the formulation is at a pH outside the buffering capacity of the buffering agent. In some embodiments, the buffering agent is acetate. In some embodiments, the acetate concentration is from 0.1 mM to 50 mM, such as from 0.5 mM to 50 mM, from 1 mM to 50 mM, or from 2.5 mM to 40 mM. In one embodiment, the acetate concentration is about 0.5 mM, about 1 mM, about 2.5 mM, about 5 mM, about 10 mM, about 20 mM, about 30 mM, or about 40 mM. The formulation can have a pH outside the buffering capacity of acetate, such as a pH above 5.8, a pH between 5.8 and 7.0, or a pH that is about 6.0, about 6.1, or about 6.2. In some embodiments, the pH is 6.0±0.3, 6.1±0.3, or 6.2±0.3.

In some embodiments, the formulation comprises a stabilizer that is an amino acid or sugar. In one embodiment, the formulation comprises two different stabilizers, such as two different sugars.

In some embodiments, the formulation comprises a surfactant, such as polysorbate 20, polysorbate 80 or Pluronic® F68. In some embodiments, the formulation does not comprise a surfactant.

In some embodiments, the formulation comprises a tonicity agent, such as sodium chloride or potassium chloride. In other embodiments, the formulation does not comprise a tonicity agent.

In some embodiments, the fusion protein is aflibercept. In some embodiments, the concentration of aflibercept is about 40 mg/ml.

BRIEF DESCRIPTION OF THE DRAWINGS

FIG. 2 shows the correlation between the target pH and the difference between the pH before buffer exchange (starting pH) and the post buffer exchange pH is shown in FIG. 2.

DETAILED DESCRIPTION

Figure 1:
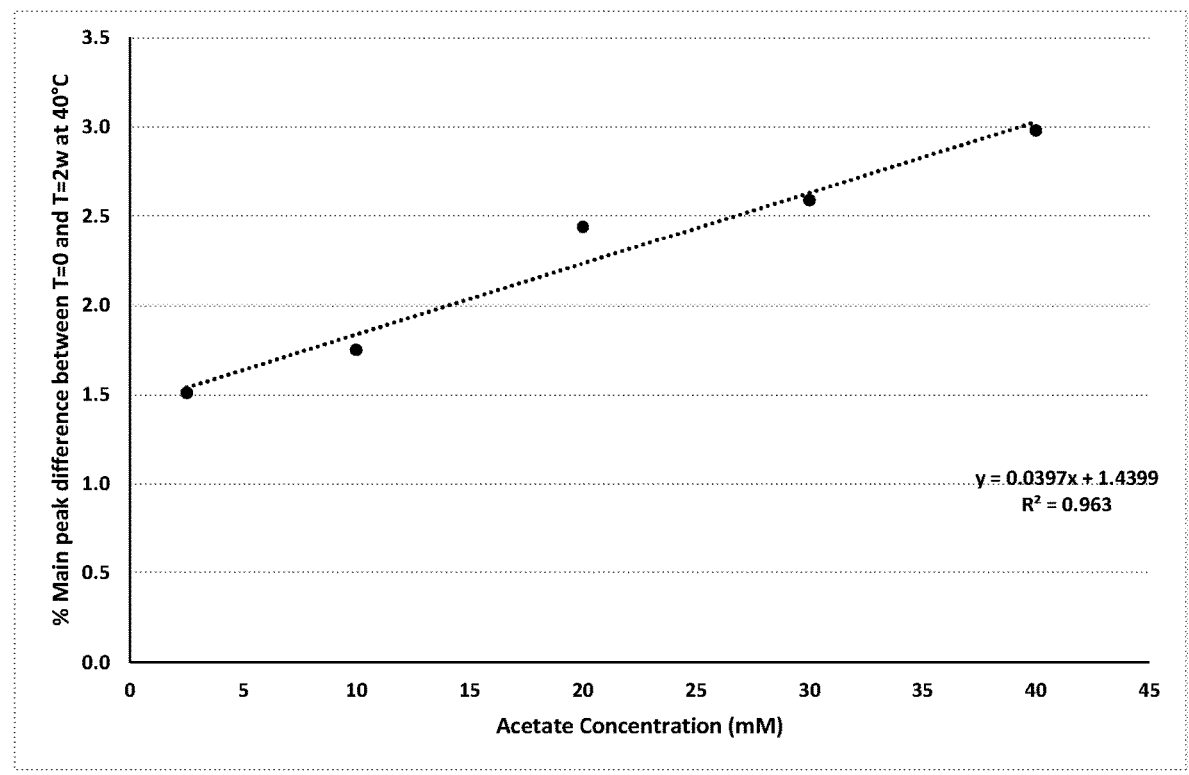
FIG. 1 shows the correlation between acetate concentration and aflibercept aggregation level as demonstrated by SE-UHPLC for the formulations as described in Example 1.

The instant disclosure provides VEGFR-Fc fusion protein formulations and methods for making and using such formulations. In some embodiments, the formulation is a buffer free formulation. In some embodiments, the formulation comprises a buffering agent and the formulation has a pH outside of the buffering capacity of the buffering agent. In some embodiments, the formulation does not comprise a buffering agent. In some embodiments, the formulation comprises a residual amount of buffering agent such that the residual amount lacks buffering capacity in the formulation.

In some embodiments, the formulation without a buffering agent is able to maintain a stable pH. For example, the formulation has a pH that is within about 0.1 or about 0.2 pH units after storage at one or two weeks at about 40° C. In some embodiments, the VEGFR-Fc fusion protein has increased stability as compared to a corresponding formulation with a buffering agent. The stability of the VEGFR-Fc fusion protein may be demonstrated by reduced aggregation levels, such as by Size Exclusion Ultra High Performance Liquid Chromatography (SEC-UHPLC). The VEGFR-Fc fusion protein can be aflibercept. In some embodiments, the concentration of the protein is about 40 mg/mL.

In some embodiments, the formulation comprises a buffering agent and has a pH that is outside the buffering capacity of the agent is able to maintain a stable pH. For example, the formulation has a pH that is within about 0.1 or about 0.2 pH units after storage at one or two weeks at about 40° C. In some embodiments, the VEGFR-Fc fusion protein has increased stability as compared to a corresponding formulation with a buffering agent (same or different buffering agent) having a pH within the buffering capacity of the agent. The stability of the VEGFR-Fc fusion protein may be demonstrated by reduced aggregation levels, such as by Size Exclusion Ultra High Performance Liquid Chromatography (SEC-UHPLC). The VEGFR-Fc fusion protein can be aflibercept. In some embodiments, the concentration of the protein is about 40 mg/mL.

In one embodiment, the formulation comprises a fusion protein comprising a domain of a vascular endothelial growth factor (VEGF) receptor and an Fc domain, a stabilizer, and optionally, a surfactant and/or a tonicity agent. In such embodiment, the formulation does not comprise a buffering agent. In some embodiments, the formulation comprises a residual amount of buffering agent such that the residual amount lacks buffering capacity in the formulation. In some embodiments, the formulation is able to maintain a stable pH. For example, the formulation has a pH that is within about 0.1 or about 0.2 pH units after storage at one or two weeks at about 40° C. In some embodiments, the VEGFR-Fc fusion protein has increased stability as compared to the same formulation but with a buffering agent. The stability of the protein may be demonstrated by reduced aggregation levels, such as by SEC-UHPLC.

In another embodiment, the formulation comprises a fusion protein comprising a domain of a vascular endothelial growth factor (VEGF) receptor and an Fc domain, a buffering agent, a stabilizer, and optionally, a surfactant and/or a tonicity agent, wherein the formulation has a pH outside the buffering capacity of the buffering agent. In some embodiments, the formulation is able to maintain a stable pH. For example, the formulation has a pH that is within about 0.1 or about 0.2 pH units after storage at one or two weeks at about 40° C. In some embodiments, the VEGFR-Fc fusion protein has increased stability as compared to the same formulation but with a buffering agent. The stability of the protein may be demonstrated by reduced aggregation levels, such as by SEC-UHPLC.

In some embodiments, the formulation comprises a fusion protein comprising a domain of a vascular endothelial growth factor (VEGF) receptor and an Fc domain, a stabilizer, and optionally, a surfactant and/or a tonicity agent, the pH is between 5.0 and 7.0, between 5.5 and 6.5 or between 5.5 and 5.6. In some embodiments, the pH is about 7.0, about 6.9, about 6.8, about 6.7, about 6.6, about 6.5, about 6.4, about 6.3, 6.2, about 6.1, about 6.0, about 5.9, about 5.8, about 5.7, about 5.6, about 5.5, about 5.4, about 5.3, about 5.2, about 5.1, or about 5.0. In some embodiments, the pH is about 6.2. In some embodiments, the pH is 7.0±0.3, 6.9±0.3, 6.8±0.3, 6.7±0.3, 6.6±0.3, 6.5±0.3, 6.4±0.3, 6.3±0.3, 6.2±0.3, 6.1±0.3, 6.0±0.3, 5.9±0.3, 5.8±0.3, 5.7±0.3, 5.6±0.3, 5.5±0.3, 5.4±0.3, 5.3±0.3, 5.2±0.3, 5.1±0.3 or 5.0±0.3. In some embodiments, the pH is 6.2±0.3.

In another embodiment, the formulation comprises a fusion protein comprising a domain of a vascular endothelial growth factor (VEGF) receptor and an Fc domain, a buffering agent, a stabilizer, and optionally, a surfactant and/or a tonicity agent, wherein the formulation has a pH outside the buffering capacity of the buffering agent. A buffering agent typically has a buffering capacity range of ±1 pH unit around its pKa value. In one embodiment, the formulation comprising a buffering agent has a pH that is greater than 1 pH unit from the pKa of the buffering agent. In some embodiments, the formulation has a pH that is at least 1.1, 1.2, 1.3, 1.4, 1.5, 1.6, 1.7, 1.8, 1.9 or 2.0 pH units from the pKa of the buffering agent. In some embodiments, the formulation has a pH that is about 1.1, about 1.2, about 1.3, about 1.4, about 1.5, about 1.6, about 1.7, about 1.8, about 1.9 or about 2.0 pH units from the pKa of the buffering agent. In one embodiment, the formulation has a pH that is about 1.4 pH units from the pKa of the buffering agent.

In one embodiment, the formulation comprising a fusion protein comprising a domain of a vascular endothelial growth factor (VEGF) receptor and an Fc domain, a buffering agent, a stabilizer, and optionally, a surfactant and/or a tonicity agent, wherein the formulation has a pH outside the buffering capacity of the buffering agent, comprises acetate as the buffering agent. The pKa value of acetate is 4.8, thus its buffering capacity is at a pH range of 3.8 to 5.8. Accordingly, in one embodiment, the formulation has a pH below 3.8 or above 5.8. In one embodiment, the pH of the formulation is above 5.8. In one embodiment, the pH is between 4.0 and 8.5, between 5.0 and 8.5, between 5.8 and 8.0, between 5.8 and 7.5, between 5.8 and 7.0, between 5.9 and 7.0, between 6.0 and 7.0, between 6.0 and 6.8, between 6.0 and 6.5, or between 6.1 and 6.5. In some embodiments, the pH is about 7.0, about 6.9, about 6.8, about 6.7, about 6.6, about 6.5, about 6.4, about 6.3, about 6.2, about 6.1, about 6.0, or about 5.9. In some embodiments, the pH is about 6.2. In some embodiments, the pH is 8.5±0.3, 8.4±0.3, 8.3±0.3, 8.2±0.3, 8.1±0.3, 8.0±0.3, 7.9±0.3, 7.8±0.3, 7.7±0.3, 7.6±0.3, 7.5±0.3, 7.4±0.3, 7.3±0.3, 7.2±0.3, 7.1±0.3, 7.0±0.3, 6.9±0.3, 6.8±0.3, 6.7±0.3, 6.6±0.3, 6.5±0.3, 6.4±0.3, 6.3±0.3, 6.2±0.3, 6.1±0.3, 6.0±0.3, 5.9±0.3, or 5.8±0.3. In some embodiments, the pH is 6.2±03.

In one embodiment, the formulation comprising a fusion protein comprising a domain of a vascular endothelial growth factor (VEGF) receptor and an Fc domain, acetate, a stabilizer, and optionally, a surfactant and/or a tonicity agent, and has a pH outside the buffering capacity of acetate (e.g., greater than 5.8, such as 6.2), the acetate is from the non-salt form of acetate. In one embodiment, the acetate is from the salt form of acetate. The buffering agent can be acetate from an acetate salt or acetic acid, such as glacial acetic acid. In one embodiment, the acetate is from sodium acetate. In one embodiment, the concentration of the acetate or acetate buffer is from 0.1 mM to 50 mM, from 0.5 mM to 50 mM, between 1 mM to 50 mM, from 1 mM to 40 mM, from 2.5 mM to 40 mM, from 1 mM to 30 mM, from 1 mM to 20 mM, from 1 mM to 10 mM, or from 1 mM to 5 mM. In one embodiment, the concentration of the acetate or acetate buffer is about 0.5 mM, about 1 mM, about 2.5 mM, about 5 mM, about 10 mM, about 20 mM, about 30 mM, about 40 mM, or about 50 mM.

In some embodiments, between 1 and 300 mg/ml of a fusion protein comprising a domain of a vascular endothelial growth factor (VEGF) receptor and an Fc domain is present in the formulations disclosed herein. In some embodiments, the formulations described herein comprises between 1 and 50 mg/ml, between 1 and 300 mg/ml, between 1 and 250 mg/ml, between 1 and 200 mg/ml, between 1 and 100 mg/ml of the fusion protein. In one embodiment, the formulation comprises between 10 and 50 mg/ml of the fusion protein. In one embodiment, the formulation comprises less than 300 mg/ml, less than 250 mg/ml, less than 200 mg/ml, less than 100 mg/ml, less than 50 mg/ml, less than 45 mg/ml, less than 40 mg/ml, less than 30 mg/ml, or less than 25 mg/ml of the fusion protein. In one embodiment, the formulation comprises about 300 mg/ml, about 250 mg/ml, about 200 mg/ml, about 100 mg/ml, about 50 mg/ml, about 45 mg m/, about 40 mg/ml, about 30 mg/ml, or about 25 mg/ml of the fusion protein. In one embodiment, the formulation comprises about 40 mg/ml of the fusion protein.

In some embodiments, the fusion protein comprises a domain of VEGFR1, a domain of VEGFR2, or a combination thereof. In some embodiments, the fusion protein comprises a domain of VEGFR1 and a domain of VEGFR2. In one embodiment, the fusion protein comprises Ig domain 2 of VEGFR1 and Ig domain 3 of VEGFR2. In one embodiment, the fusion protein comprises Ig domain 2 of VEGFR1, Ig domain 3 of VEGFR2, and an Fc domain of IgG1. In one embodiment, the fusion protein is a VEGF Trap. In another embodiment, the fusion protein is aflibercept. In another embodiment, the fusion protein comprises an amino acid sequence of SEQ ID NO: 1. In another embodiment, the fusion protein comprises an amino acid sequence of SEQ ID NO: 2. In one embodiment, the formulation comprises about 40 mg/ml of aflibercept. In one embodiment, the formulation comprises about 40 mg/ml of a fusion protein comprising a protein having an amino acid sequence of SEQ ID NO: 1 or SEQ ID NO: 2. In one embodiment, the formulation comprises about 40 mg/ml of a fusion protein comprising a protein having an amino acid sequence of SEQ ID NO: 1 and a fusion protein comprising a protein having an amino acid sequence of SEQ ID NO: 2.

```
                                                SEQ ID NO: 1
SDTGRPFVEMYSEIPEIIHMIEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDFNVVEYPSSKHQHKK

LVNRDLKTQSGSEMKKFLSTLTIDGVTRSDQGLYTCAASSGLMTKKNSTF

VRVHEKDKTHTCPPCPAPELLGGPSVFLFPPKPKDTLMISRTPEVTCVVV

DVSHEDPEVKFNVVYVDGVEVHNAKTKPREEQYNSTYRVVSVLTVLHQDW

LNGKEYKCKVSNKALPAPIEKTISKAKGQPREPQVYTLPPSRDELTKNQV

SLTCLVKGFYPSDIAVEWESNGQPENNYKTTPPVLDSDGSFFLYSKLTVD

KSRWQQGNVFSCSVMHEALHNHYTQKSLSLSPG

SEQ ID NO: 2
SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDFNWEYPSSKHQEIKK

LVNRDLKTQSGSEMKKFLSTLTIDGVTRSDQGLYTCAASSGLMTKKNSTF

VRVHEKDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDWL

NGKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVDK

SRWQQGNVFSCSVMHEALHNHYTQKSLSLSPGK (SEQ ID NO: 2)
```

In one embodiment, the formulation comprises a fusion protein comprising a domain of a vascular endothelial growth factor (VEGF) receptor and an Fc domain (e.g., aflibercept, such as about 40 mg/ml of aflibercept), a buffering agent (e.g., acetate, such as between 2.5 mM to 40 mM of acetate), a stabilizer, and optionally, a surfactant, wherein the pH is outside the buffering capacity of the buffering agent (e.g., greater than 5.8, such as about 6.2, when the buffering agent is acetate), wherein the stabilizer is an amino acid or sugar. In one embodiment, the formulation comprises a fusion protein comprising a domain of a vascular endothelial growth factor (VEGF) receptor and an Fc domain (e.g., aflibercept, such as about 40 mg/ml of aflibercept), a stabilizer, and optionally, a surfactant, wherein the stabilizer is an amino acid or sugar.

In one embodiment, the stabilizer is an amino acid. In one embodiment, the amino acid is proline. In another embodiment, the amino acid is glycine. In some embodiments, the amino acid is a basic amino acid, such as arginine or lysine. In other embodiments, the amino acid is an acidic amino acid, such as aspartic acid. In yet other embodiments, the amino acid is a hydrophobic amino acid, such as alanine. In some embodiments, the formulation comprises two different amino acids. In one embodiment, the stabilizer is a sugar. The sugar can be sucrose, sorbitol, glycerol, trehalose (e.g., α,α-trehalose or trehalose dihydrate), mannitol, dextrose, dextran, glucose or any combination thereof. In one embodiment, the stabilizer is sucrose. In another embodiment, the stabilizer is trehalose. In another embodiment, the stabilizer is a cyclodextrin, such as hydroxypropyl-β-cyclodextrin (HPBCD). In yet another embodiment, the formulation comprises two different sugars, such as sucrose and trehalose. In another embodiment, the stabilizer is cyclodextrin. In yet another embodiment, the formulation comprises one or more sugars and one or more amino acids.

The concentration of the stabilizer can be between 1 mM to 300 mM, between 10 mM to 300 mM, between 100 mM to 300 mM, between 200 mM to 300 mM, and between 200 mM and 280 mM. In one embodiment, the concentration of the stabilizer is about 200 mM, such as about 200 mM proline. In another embodiment, the concentration of the stabilizer is about 280 mM, such as about 280 mM glycine.

In yet other embodiments, the formulation comprises between 0 and 50% (w/v) of the stabilizer. In some embodiments, the formulation comprises between 0 and 20% (w/v) of the stabilizer. In some embodiments, the formulation comprises between 0 and 10% (w/v), between 5 and 10% (w/v) or between 2 and 10% (w/v) of a stabilizer. In some embodiments, the formulation comprises about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, or about 10% (w/v) of a stabilizer, such as a sugar. The sugar can be sucrose or trehalose. In one embodiment, the formulation comprises about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5% or about 10% (w/v) of sucrose. In one embodiment, the formulation comprises about 5% sucrose. In yet another embodiment, the formulation comprises about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5% or about 10% (w/v) of trehalose. In one embodiment, the formulation comprises about 3% (w/v) trehalose. In one embodiment, the formulation comprises about 3.5% (w/v) trehalose. In one embodiment, the formulation comprises about 4% (w/v) trehalose. In one embodiment, the formulation comprises about 4.5% (w/v) trehalose. In one embodiment, the formulation comprises about 5% (w/v) trehalose. In another embodiment, the formulation comprises about 6.5% (w/v) trehalose.

In one embodiment, the formulation comprises two different sugars. In one embodiment, the concentration of the first sugar and the second sugar is each between 0 and 10% (w/v), between 5 and 10% (w/v) or between 2 and 10% (w/v). In one embodiment, the total concentration of the first sugar and the second sugar is between 0 and 10% (w/v), between 5 and 10% (w/v) or between 2 and 10% (w/v). In another embodiment, the concentration of the first sugar is about 1.5%, about 2%, about 2.5%, about 3%, about 3.5%, about 4% or about 5% (w/v). In another embodiment, the concentration of the second sugar is about 1.5%, about 2%, about 2.5%, about 3%, about 3.5%, 4% or about 5% (w/v). In one embodiment, the first sugar is sucrose and the second sugar is trehalose. In yet another embodiment, the formulation comprises about 1.5%, about 2%, about 2.5%, about 3%, about 3.5%, about 5%, about 6%, about 6.5%, about 7%, about 7.5%, about 8%, about 8.5%, about 9%, or about 10% (w/v) of sucrose and trehalose, such as about 1% (w/v) sucrose and about 7% (w/v) trehalose, about 2% (w/v) sucrose and about 6% (w/v) trehalose, about 3% (w/v) sucrose and about 5% (w/v) trehalose, about 4% (w/v) sucrose and about 4% (w/v) trehalose, about 5% (w/v) sucrose and about 3% (w/v) trehalose, about 6% (w/v) sucrose and about 2% (w/v) trehalose, or about 7% (w/v) sucrose and about 1% (w/v) trehalose. In another embodiment, the formulation comprises about 5% (w/v) sucrose and about 3.5% (w/v) trehalose, about 5% (w/v) sucrose and about 4% (w/v) trehalose, about 5% (w/v) sucrose and about 2.5% (w/v) trehalose, about 5% (w/v) sucrose and about 2% (w/v) trehalose, about 5% (w/v) sucrose and about 1.5% (w/v) trehalose, or about 4% (w/v) sucrose and about 2.5% (w/v) trehalose.

In one embodiment, the formulation does not comprise a surfactant. In another embodiment, the formulation comprises a fusion protein comprising a domain of a vascular endothelial growth factor (VEGF) receptor and an Fc domain (e.g., aflibercept, such as about 40 mg/ml of aflibercept), a buffering agent (e.g., acetate, such as between 2.5 mM to 40 mM of acetate), a stabilizer (e.g., sucrose and/or trehalose), and a surfactant, wherein the pH is outside the buffering capacity of the buffering agent (e.g., greater than 5.8, such as about 6.2, when the buffering agent is acetate).

In one embodiment, the formulation comprises a fusion protein comprising a domain of a vascular endothelial growth factor (VEGF) receptor and an Fc domain (e.g., aflibercept, such as about 40 mg/ml of aflibercept), a stabilizer (e.g., sucrose and/or trehalose), and a surfactant. The surfactant can be a polyoxyethylene glycol alkyl ether, a polyoxypropylene glycol alkyl ether, a glucoside alkyl ether, a polyoxyethylene glycol octylphenol ether, a polyoxyethylene glycol alkylphenol ether, a glycerol alkyl ester, a polyoxyethylene glycol sorbitan alkyl ester, a sorbitan alkyl ester, a cocamide MEA, a cocamide DEA, a dodecyldimethylamine oxide, a poloxamer, a polyethoxylated tallow amine (POEA), or a combination thereof. In one embodiment, the surfactant is a polysorbate. In one embodiment, the surfactant is polysorbate 20. In another embodiment, the surfactant is polysorbate 80. In yet another embodiment, the surfactant is a poloxamer, such as poloxamer 188. In one embodiment, the surfactant is Pluronic® F-68. In some embodiments, the formulation comprises from 0.001 to 3% (w/v), 0.001 to 2% (w/v), 0.001 to 1% (w/v), 0.001 to 0.5% (w/v) or 0.01% to 0.1% (w/v) of a surfactant. In some embodiments, the formulation comprises about 0.03% (w/v) of a surfactant, such as polysorbate 80. In some embodiments, the formulation comprises about 0.02% (w/v) of a surfactant, such as polysorbate 20. In some embodiments, the formulation comprises about 0.01% (w/v) of a surfactant, such as polysorbate 80. In some embodiments, the formulation comprises about 0.005% (w/v) of a surfactant, such as polysorbate 80. In some embodiments, the formulation comprises about 0.03% (w/v) of a surfactant, such as polysorbate 20. In some embodiments, the formulation comprises about 0.02% (w/v) of a surfactant, such as polysorbate 20. In some embodiments, the formulation comprises about 0.01% (w/v) of a surfactant, such as polysorbate 20. In some embodiments, the formulation comprises about 0.1% (w/v) of a surfactant, such as Pluronic® F-68.

In one embodiment, the formulation comprises acetate, sucrose, trehalose, and a surfactant. In one embodiment, the formulation comprises about 2.5 mM acetate, about 5% (w/v) sucrose, about 3.5% (w/v) trehalose, and about 0.01% (w/v) polysorbate 80, at a pH of about 6.2. In one embodiment, the formulation comprises about 2.5 mM acetate, about 5% (w/v) sucrose, about 3% (w/v) trehalose, about 5 mM NaCl, and about 0.01% (w/v) polysorbate 80, at a pH of about 6.2.

In one embodiment, the formulation does not comprise a buffering agent. In some embodiments, the formulation comprises a residual amount of buffering agent such that the residual amount lacks buffering capacity in the formulation. In one embodiment, the formulation comprises about 5%

(w/v) sucrose, about 3.5% (w/v) trehalose, and about 0.01% (w/v) of a surfactant (e.g., a polysorbate), at a pH of about 6.2. In one embodiment, the formulation comprises about 5% (w/v) sucrose, about 3.5% (w/v) trehalose, and about 0.02% (w/v) of a surfactant (e.g., a polysorbate), at a pH of about 6.2. In one embodiment, the formulation comprises about 5% (w/v) sucrose, about 3.5% (w/v) trehalose, and about 0.03% (w/v) of a surfactant (e.g., a polysorbate), at a pH of about 6.2. In one embodiment, the formulation comprises about 5% (w/v) sucrose, about 3.5% (w/v) trehalose, and about 0.01% (w/v) polysorbate 80, at a pH of about 6.2. In one embodiment, the formulation comprises about 5% (w/v) sucrose, about 3.5% (w/v) trehalose, and about 0.02% (w/v) polysorbate 80, at a pH of about 6.2. In one embodiment, the formulation comprises about 5% (w/v) sucrose, about 3.5% (w/v) trehalose, and about 0.03% (w/v) polysorbate 20, at a pH of about 6.2. In one embodiment, the formulation comprises about 5% (w/v) sucrose, about 3% (w/v) trehalose, about 5 mM sodium chloride, and about 0.01% (w/v) of a surfactant (e.g., a polysorbate), at a pH of about 6.2. In one embodiment, the formulation comprises about 5% (w/v) sucrose, about 3% (w/v) trehalose, about 5 mM sodium chloride, and about 0.01% (w/v) polysorbate 80, at a pH of about 6.2.

In one embodiment, the formulation does not comprise a tonicity agent. In another embodiment, the formulation comprises a fusion protein comprising a domain of a vascular endothelial growth factor (VEGF) receptor and an Fc domain (e.g., aflibercept, such as about 40 mg/ml of aflibercept), a buffering agent (e.g., acetate, such as between 2.5 mM to 40 mM of acetate), a stabilizer (e.g., sucrose and/or trehalose), and a tonicity agent, wherein the pH is outside the buffering capacity of the buffering agent (e.g., greater than 5.8, such as about 6.2, when the buffering agent is acetate). In another embodiment, the formulation comprises a fusion protein comprising a domain of a vascular endothelial growth factor (VEGF) receptor and an Fc domain (e.g., aflibercept, such as about 40 mg/ml of aflibercept), a buffering agent (e.g., acetate, such as between 2.5 mM to 40 mM of acetate), a stabilizer (e.g., sucrose and/or trehalose), a tonicity agent, and a surfactant, wherein the pH is outside the buffering capacity of the buffering agent (e.g., greater than 5.8, such as about 6.2, when the buffering agent is acetate). In one embodiment, the formulation comprises a fusion protein comprising a domain of a vascular endothelial growth factor (VEGF) receptor and an Fc domain (e.g., aflibercept, such as about 40 mg/ml of aflibercept), a stabilizer (e.g., sucrose and/or trehalose), and a tonicity agent. In another embodiment, the formulation comprises a fusion protein comprising a domain of a vascular endothelial growth factor (VEGF) receptor and an Fc domain (e.g., aflibercept, such as about 40 mg/ml of aflibercept), a stabilizer (e.g., sucrose and/or trehalose), a tonicity agent, and a surfactant (e.g., a polysorbate).

The concentration of the tonicity agent can be between 1 mM to 250 mM, between 5 mM to 200 mM, between 40 mM to 200 mM, or between 40 mM to 150 mM. In one embodiment, the concentration of the tonicity agent is about 1 mM, about 5 mM, about 10 mM, about 20 mM, about 30 mM, about 40 mM, about 50 mM, about 100 mM, about 140 mM or about 150 mM. The tonicity agent can be a salt, such as a chloride salt. In one embodiment, the tonicity agent is sodium chloride. In another embodiment, the tonicity agent is potassium chloride.

In some embodiments, a formulation disclosed herein may comprise am additional excipient. In one embodiment, the formulation can further comprise a polymeric excipient, such as hyaluronic acid, carboxymethylcellulose sodium (CMC), or poly(lactic-co-glycolic acid) (PLGA).

In some embodiments, the formulations disclosed herein are used for intravitreal administration, such as for the treatment of an ocular condition such as wet type age related macular degeneration (AMD). In some embodiments, the condition is macular edema following retinal vein occlusion (RVO) or diabetic retinopathy (DR). In yet other embodiments, the condition cause blindness. In one embodiment, the formulation is capable to be used with a prefilled syringe. In one embodiment, the prefilled syringe is for intravitreal administration of the formulation.

In some embodiments, the formulation disclosed herein has a particulate count (e.g., subvisible particle level or count) of less than 100 particles, less than 75 particles, less than 50 particles, less than 25 particles, less than 20 particles, less than 15 particles, less than 10 particles, less than 5 particles, or less than 2 particles, per one milliliter, for a particle size of >10 µm. In some embodiments, the formulation disclosed herein has a particulate count of less than 100 particles, less than 75 particles, less than 50 particles, less than 25 particles, less than 20 particles, less than 15 particles, less than 10 particles, less than 5 particles, or less than 2 particles, per one milliliter for a particle size of ≥25 µm. In some embodiments, the formulation disclosed herein has a particulate count of less than 100 particles, less than 75 particles, less than 50 particles, less than 25 particles, less than 20 particles, less than 15 particles, less than 10 particles, less than 5 particles, or less than 2 particles, per one milliliter, for a particle size of ≥50 µm. In some embodiments, the formulation disclosed herein has a particulate count of less than 50 particles per one milliliter for particle size of ≥10 µm. In some embodiments, the formulation disclosed herein has a particulate count of less than 5 particles per one milliliter for particle size of ≥25 µm. In some embodiments, the formulation disclosed herein has a particulate count of less than 2 particles per one milliliter for particle size of ≥50 µm. In some embodiments, the formulation disclosed herein has a particulate count of no more than an average of 50 particles per one milliliter for particle size of ≥10 µm. In some embodiments, the formulation disclosed herein has a particulate count of no more than an average of 5 particles per one milliliter for particle size of ≥25 µm. In some embodiments, the formulation disclosed herein has a particulate count of no more than an average of 2 particles per one milliliter for particle size of ≥50 µm.

In some embodiments, the particulate count is determined by light obscuration, such as through the use of a liquid particle counter, such as a commercially available counter developed by HIAC. In some embodiments, the particulate count is determined at a temperature of 25° C. In some embodiments, a first formulation (e.g., a formulation without a buffer or a formulation with a buffer, in which the pH of the formulation is outside the buffering capacity of the buffer) is determined to be more desirable than a second formulation (e.g., a formulation with a buffer, in which the pH of the formulation is within the buffering capacity of the buffer) when there are fewer particulate counts or lower subvisible particle counts in the first formulation as compared to the second formulation. In another embodiment, a first formulation has similar particulate counts or subvisible particle counts (e.g., a lack of significance difference) as the second formulation.

In some embodiments, a first formulation (e.g., a formulation without a buffer or a formulation with a buffer, in which the pH of the formulation is outside the buffering capacity of the buffer) is determined to be more stable than a second formulation (e.g., a formulation with a buffer, in which the pH of the formulation is within the buffering capacity of the buffer) when the fusion protein of the first formulation retains more of its original characateristics or properties than the fusion protein of the second formulation after one or more process stresses and/or after storage for a given time period. Stability of a formulation can be determined by analyzing the properties or characteristics of the protein such as known in the art, for example, as described in U.S. Pat. Nos. 8,092,803 and 9,982,032, and PCT Publications WO2017129685 and WO2018094316.

In one embodiment, a first formulation (e.g., a formulation without a buffer or a formulation with a buffer, in which the pH of the formulation is outside the buffering capacity of the buffer) is determined to be more stable than a second formulation (e.g., a formulation with a buffer, in which the pH of the formulation is within the buffering capacity of the buffer) when the first formulation has less aggregation than the second formulation after one or more process stresses or stress conditions, such as known in the art, e.g., as described in WO2017129685. In one embodiment, the stress condition is shaking. In another embodiment, the stress condition is one or more freeze/thaw cycles, such as one, two, three, four or five freeze/thaw cycles. In another embodiment, the stress condition is vibration, pressure, and/or drop-shock. In one embodiment, the stress condition is photoexposure. In one embodiment, the stress condition is mixing. In one embodiment, the formulation is subjected to any one or more of the stress conditions. The stress conditions can comprise shaking, one or more freeze/thaw cycle(s), filtration, mixing, photoexposure, vibration, pressure, drop-shock stress, and/or any combination thereof. In one embodiment, the stress process comprises shaking (e.g., at 300 rpm at 25° C. for seven days); three freeze/thaw cycles from 25° C. to –20° C. with a rate of 1° C./min, and after each cooling/heating step the temperature is kept constant for ten minutes. In another embodiment, the stress process comprises three freeze/thaw cycles between 25° C. to –30° C.; filtration through a 0.2 μm PVDF filter; optionally, mixing; holding at 2° C. to 8° C., photoexposure, and a full transportation simulation (e.g., with a time sequence of more than 24 hours, 48 hours, 72 hours, 96 hours, or 110 hours, or between 24 and 110 hours, between 48 and 96 hours, such as about 50 hours, about 60 hours, about 70 hours, about 80 hours, about 90 hours, about 100 hours or about 100 hours, which includes vibration, pressure and drop-shock stresses).

In another embodiment, a first formulation (e.g., a formulation without a buffer or a formulation with a buffer, in which the pH of the formulation is outside the buffering capacity of the buffer) is determined to be more stable than a second formulation (e.g., a formulation with a buffer, in which the pH of the formulation is within the buffering capacity of the buffer) when the first formulation has less aggregation than the second formulation after storage for about 1 week, about two weeks, about 3 weeks, about 4 weeks, about 3 months, about 4 months, about 5 months, about 6 months, about 7 months, about 8 months, about 9 months, about 10 months, about 11 months, about 12 months, about 15 months, about 18 months, about 21 months, about 24 months, about 30 months, or about 36 months. Storage can be at a given temperature, e.g., about 40° C., about 30° C., about 25° C., about 5° C., about –20° C. or about –30° C.

In one embodiment, a first formulation (e.g., a formulation without a buffer or a formulation with a buffer, in which the pH of the formulation is outside the buffering capacity of the buffer) is more stable than a second formulation (e.g., a formulation with a buffer, in which the pH of the formulation is within the buffering capacity of the buffer) when the first formulation has less aggregation than the second formulation after one or more process stresses and storage for a given time period (e.g., about 1 week, about two weeks, about 3 weeks, about 4 weeks, about 3 months, about 4 months, about 5 months, about 6 months, about 7 months, about 8 months, about 9 months, about 10 months, about 11 months, about 15 months, about 18 months, about 21 months, about 24 months, about 30 months, or about 36 months, at about 40° C., about 30° C., about 25° C., about 5° C., about –20° C. or about –30° C.).

The stability of a formulation can be determined by any method known in the art, such as described in U.S. Pat. Nos. 8,092,803 and 9,982,032, and PCT Publications WO2017129685 and WO2018094316. In one embodiment, stability of a formulation is determined by chromatography, such as size exclusion chromatography, e.g., size exclusion high performance liquid chromatography (SE-HPLC) or size exclusion ultra high performance liquid chromatography (SE-UHPLC), or hydrophobic high performance liquid chromatography (HI-HPLC), in which a lower change or difference in a first peak from a first formulation before a stress process and/or storage condition as compared to a second peak from the same formulation after the stress process and/or storage condition as compared to a second formulation with a greater change or difference in its first and second peaks before and after a stress process and/or storage condition, respectively, indicates the first formulation is more stable than the second formation.

In another embodiment, stability of a formulation is determined by the turbidity of the formulation (e.g., such as measured at $OD_{405}$ nm), percent of protein recovered (e.g., determined by size exclusion HPLC (SE-HPLC)), and/or purity of protein (e.g., determined by SE-HPLC), in which lower turbidity, higher percentage of recovery and higher purity indicates higher stability. In some embodiments, SDS-PAGE (reducing or non-reducing) is used to determine the stability of a formulation. In some embodiments, asymmetric flow field-flow fractionation (AF4) is used. In other embodiments, isoelectric focusing (IEF), e.g., capiliary isoelectric focusing (cIEF), is used. Increased fragments and/or changes in IEF in a first formulation as compared to a second formulation would indicate the first formulation is less stable. Any one method or combination of methods can be used to determine the stability of a formulation.

The detailed description and following examples illustrate the present invention and are not to be construed as limiting the present invention thereto. Various changes and modifications can be made by those skilled in the art on the basis of the description of the invention, and such changes and modifications are also included in the present invention.

EXAMPLES

Example 1

Aflibercept Stability of Acetate Formulations at pH 6.2

The stability of aflibercept was tested in acetate formulations of varying concentrations at a pH outside the ideal buffering capacity of acetate. The pKa value of acetate is 4.8, with a buffering capacity at a pH range of about 3.8 to about 5.8 as a buffering agent has a buffering capacity range of approximately ±1 pH unit around its pKa value. The acetate concentration was varied to examine the impact of the acetate concentration on the ability to maintain the pH and the stability profile of aflibercept. Eylea® is formulated as 40 mg/mL aflibercept in 10 mM sodium phosphate, 40 mM sodium chloride, 5% sucrose, 0.03% polysorbate 20 at a pH of 6.2, and this formulation was included for comparison (Formulation 8).

Forty mg/ml of aflibercept was buffer exchanged with the formulations specified in Table 1. Surfactant was added to the different formulations post the buffer exchange. The performance of the buffer exchange was verified by testing osmolality, protein concentration and pH. Each formulation underwent filtration, three freeze-thaw cycles and drop-shock process stresses prior to being stored at the stress condition of 40° C. for up to two weeks.

buffering agent) was able to maintain the pH to the same extent as a formulation with an active buffering agent.

To determine the protein stability of the formulations described in Table 1, the formulations were tested by Size Exclusion Ultra High Performance Liquid Chromatography (SE-UHPLC) to analyze the aggregation pattern post the buffer exchange and during storage. SEC-UHPLC separates proteins based on differences in their hydrodynamic volumes. Molecules with larger hydrodynamic volumes elute earlier than molecules with smaller volumes. The samples were loaded onto an SE-UHPLC column, separated isocratically and the eluent monitored by UV absorbance. Purity was determined by calculating the percentage of each separated component as compared to the total integrated area.

TABLE 1

Formulations 1-8.

| Formulation | Aflibercept (mg/mL) | Buffering Agent | Tonicity Agent | Stabilizer | Surfactant | pH |
|---|---|---|---|---|---|---|
| 1 | 40 | 2.5 mM acetate | | 5% sucrose + 3.5% α,α-trehalose | 0.01% PS80 | 6.2 |
| 2 | 40 | 10 mM acetate | | 5% sucrose + 3% α,α-trehalose | 0.01% PS80 | 6.2 |
| 3 | 40 | 20 mM acetate | | 5% sucrose + 2.5% α,α-trehalose | 0.01% PS80 | 6.2 |
| 4 | 40 | 30 mM acetate | | 5% sucrose + 2% α,α-trehalose | 0.01% PS80 | 6.2 |
| 5 | 40 | 40 mM acetate | | 5% sucrose + 1.5% α,α-trehalose | 0.01% PS80 | 6.2 |
| 6 | 40 | 40 mM acetate | | 4% sucrose + 2.5% α,α-trehalose | 0.01% PS80 | 6.0 |
| 7 | 40 | 40 mM acetate | | 6.5% α,α-trehalose | 0.01% PS80 | 6.2 |
| 8 | 40 | 10 mM Sodium phosphate | 40mM NaCl | 5% Sucrose | 0.03% PS20 | 6.2 |

The pH for each formulation in Table 1 was determined at timepoints 0, 1 week, and 2 weeks and is shown in Table 2. The pH difference or delta between the pH at T=0 and T=1 week and between T=0 and T=2 weeks for the formulations is also shown in Table 2.

The higher the main peak value (e.g., percentage) determined by SEC-UHPLC for a formulation, the more stable the formulation, as it indicates a lower level of aggregation. Another indication of increased stability is a lack of change

TABLE 2 pH Values Post Buffer Exchange and Storage at 40° C. for Formulations 1-8.

| Formulation | T = 0 | T = 1 week | Delta from T = 0 | T = 2 weeks | Delta from T = 0 |
|---|---|---|---|---|---|
| 1 | 6.1 | 6.2 | 0.1 | 6.2 | 0.1 |
| 2 | 6.1 | 6.2 | 0.1 | 6.3 | 0.2 |
| 3 | 6.1 | 6.1 | 0.1 | 6.2 | 0.1 |
| 4 | 6.0 | 6.1 | 0.1 | 6.2 | 0.1 |
| 5 | 6.0 | 6.1 | 0.1 | 6.1 | 0.1 |
| 6 | 5.9 | 6.0 | 0.0 | 6.0 | 0.1 |
| 7 | 6.1 | 6.1 | 0.1 | 6.2 | 0.1 |
| 8 | 6.2 | 6.2 | 0.0 | 6.3 | 0.1 |

As shown in Table 2, the pH difference between T=0 and following two weeks of storage at 40° C. was a maximum of 0.2 pH units, a pH shift that is within typical manufacturing variability (usually ±0.3 pH units) and is not expected to impact the quality attributes of aflibercept. Moreover, Formulation 8, which includes a buffering agent within its buffering capacity pH, also demonstrated a shift of 0.1 pH units. Thus, a formulation without an active buffering agent (i.e., a formulation with a buffering agent but at a pH outside of the buffering capacity of the agent, therefore not an active in the main peak value between an initial timepoint and a later timepoint as compared to another formulation.

The percentage of the main peak for each formulation in Table 1 was determined at timepoints 0, 1 week, and 2 weeks for the formulations stored at 40° C., as shown in Table 3. The difference or delta value between the main peak percentages of T=0 and T=1 week and between the main peak percentages of T=0 and T=2 weeks for the formulations is also shown in Table 3.

TABLE 3

SEC-UHPLC Main Peak Results for Formulations 1-8.

| % Main Peak | T = 0 | T = 1 week | Delta from T = 0 | T = 2 weeks | Delta from T = 0 |
|---|---|---|---|---|---|
| 1 | 98.5 | 97.6 | 0.9 | 97.0 | 1.5 |
| 2 | 98.5 | 97.4 | 1.1 | 96.7 | 1.8 |
| 3 | 98.5 | 97.1 | 1.4 | 96.0 | 2.4 |
| 4 | 98.5 | 97.0 | 1.5 | 95.9 | 2.6 |
| 5 | 98.5 | 96.7 | 1.7 | 95.5 | 3.0 |
| 6 | 98.5 | 96.7 | 1.8 | 95.3 | 3.2 |
| 7 | 98.4 | 96.7 | 1.8 | 95.4 | 3.0 |
| 8 | 98.4 | 95.7 | 2.7 | 93.8 | 4.6 |

An improved stability profile is demonstrated by a reduction in aggregation levels, thus a higher main peak value and a lower delta value. Surprisingly, all acetate buffer formulations, which were at a pH outside of the ideal buffering capacity pH range of acetate (Formulations 1-7) demonstrated reduced aggregation levels in comparison to the phosphate buffer formulation, which was at a pH within the ideal buffering capacity pH range of phosphate (Formulation 8). The results also surprisingly demonstrated a strong correlation between a reduced acetate concentration and a reduction in aggregation levels, thus an increase in aflibercept stability, as shown in FIG. 1.

Example 2

Aflibercept Stability of Formulations without a Buffering Agent

Example 1 demonstrated that the stability of aflibercept, as determined by aggregation levels, is improved with lower acetate concentrations in a formulation with a pH outside of the ideal buffering capacity range of acetate. Thus, formulations without a buffering agent were tested to determine the stability of aflibercept in formulations without a buffering agent.

To test the stability of aflibercept and the ability of the formulation to reach and maintain a target pH in a formulation without the presence of a buffering agent, aflibercept was purified from a cell culture using CEX column into a 100 mM Na acetate, 300 mM NaCl, pH 5.0 at 3.6 mg/mL. The target pH of the composition was pH 5.0, 5.5, 5.8, 6.2, 6.4 or 6.8, respectively. However, when titrated, the pH were: 5.0, 5.5, 6.0, 6.2, 6.5, and 6.9, respectively (Table 4). The protein was then concentrated to 40 mg/mL and buffer exchanged with a 5% sucrose, 5% trehalose formulation buffer. The pH and protein concentration post buffer exchange were tested and the samples were stored at the stress condition of 40° C. for up to two weeks.

TABLE 4

Formulations I-IV.

| Formulation | Aflibercept (mg/mL) | Stabilizer A | Stabilizer B | Target pH (Titrated pH) |
|---|---|---|---|---|
| I | 40 | 5% sucrose | 5% trehalose | 5.0 (5.0) |
| II | 40 | 5% sucrose | 5% trehalose | 5.5 (5.5) |
| III | 40 | 5% sucrose | 5% trehalose | 5.8 (6.0) |
| IV | 40 | 5% sucrose | 5% trehalose | 6.2 (6.2) |
| V | 40 | 5% sucrose | 5% trehalose | 6.4 (6.5) |
| VI | 40 | 5% sucrose | 5% trehalose | 6.8 (6.9) |

Figure 2A:
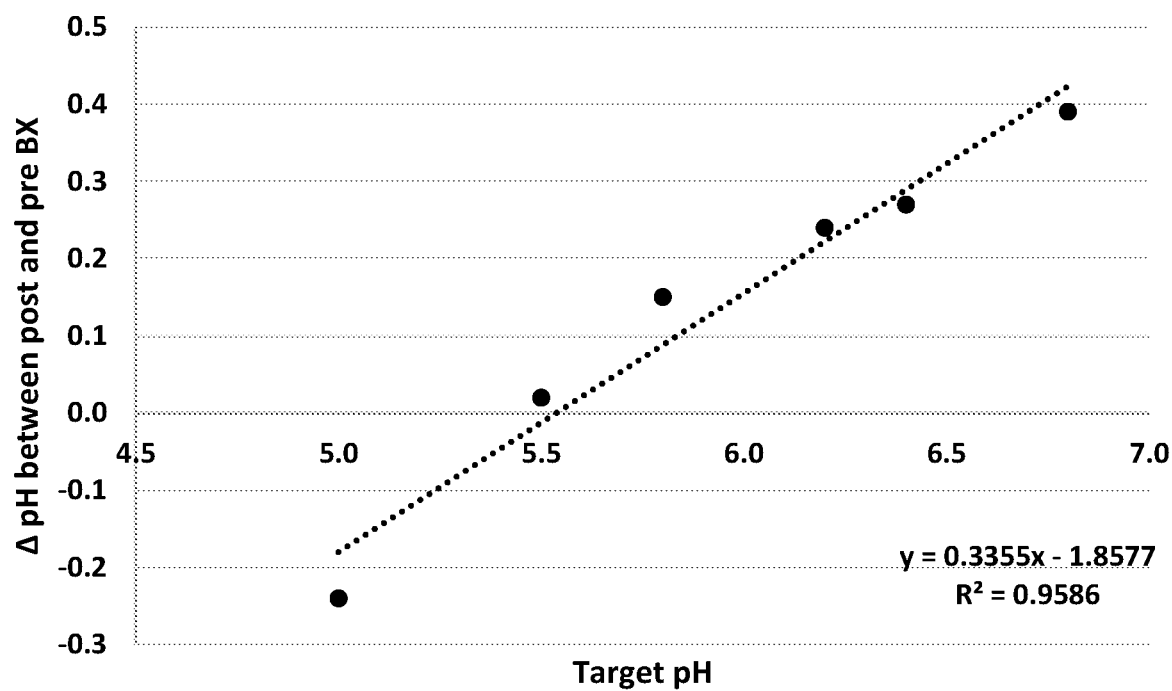
(FIG. 2A shows the correlation with the target pH.
Figure 2B:
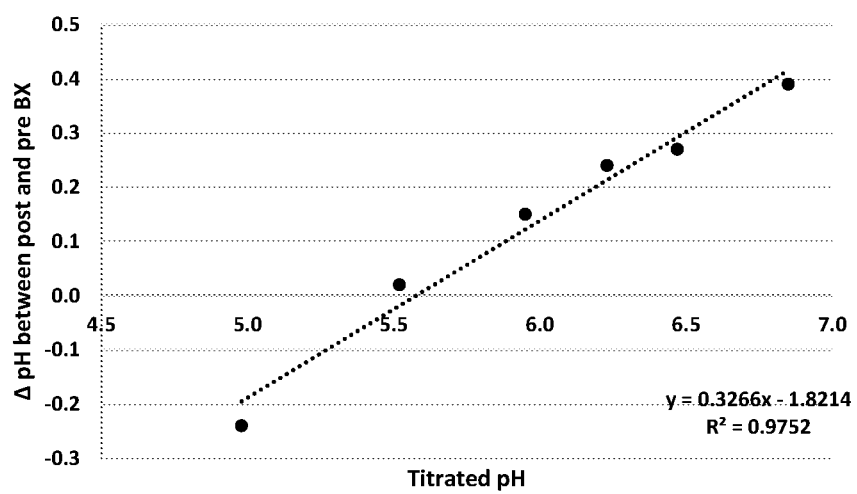
FIG. 2B shows the correlation with the titrated pH).

The correlation between the target pH and the difference between the pH before buffer exchange (starting pH) and the post buffer exchange pH is shown in FIG. 2 (FIG. 2A shows the correlation with the target pH, FIG. 2B shows the correlation with the titrated pH). There was a difference of up to 0.4 units between the starting pH and the pH post the buffer exchange. The difference between the starting pH and the pH following the buffer exchange has a linear correlation as shown in FIG. 2B. Thus, the target pH can be obtained by adjusting the starting pH.

The pH for each formulation in Table 4 prior to buffer exchange, post buffer exchange and UF/DF, at 1 week and at 2 weeks at 40° C. is shown in Table 5.

TABLE 5 pH Values Post Buffer Exchange and Storage at 40° C. for Formulations I-VI.

| Formulation | Starting pH | Post Buffer Exchange UF/DF pH (T = 0) | pH after 1 week | pH after 2 weeks |
|---|---|---|---|---|
| I | 5.0 | 5.2 | 5.2 | 5.1 |
| II | 5.5 | 5.5 | 5.5 | 5.4 |
| III | 6.0 | 5.8 | 5.8 | 5.6 |
| IV | 6.2 | 6.0 | 6.0 | 5.8 |
| V | 6.5 | 6.2 | 6.2 | 6.0 |
| VI | 6.8 | 6.5 | 6.4 | 6.3 |

The pH remained stable over storage at stress conditions as shown in Table 5. The pH of the formulations remained the same after one week of storage at 40° C. except for a 0.1 unit decrease for formulation VI. After two weeks at 40° C. the pH decreased by 0.1 to 0.2 units, a pH shift that is within typical manufacturing variability (usually ±0.3 pH units) and is not expected to impact the quality attributes of aflibercept.

To determine the stability of the formulations described in Table 4, the formulations were tested by SEC-UHPLC, as described in Example 1. The higher the main peak value (e.g., percentage) determined by SEC-UHPLC for a formulation, the more stable the formulation, as it indicates a lower level of aggregation. Another indication of increased stability is a lack of change in the main peak value between an initial timepoint and a later timepoint as compared to another formulation.

The percentage of the main peak for each formulation in Table 4 was determined at timepoints 0, 1 week, and 2 weeks (T=0, T=1 w, T=2 w, respectively) for the formulations stored at 40° C., as shown in Table 6. The difference or delta value between the main peak percentages of T=0 and T=1 week and between the main peak percentages of T=0 and T=2 weeks for the formulations is also shown in Table 6.

TABLE 6

SEC-UHPLC Main Peak Results for Formulations I-VI.

| Formulation | T = 0 | T = 1 week | Delta from T = 0 | T = 2 weeks | Delta from T = 0 |
|---|---|---|---|---|---|
| I | 98.8 | 98.1 | 0.6 | 96.3 | 2.5 |
| II | 98.5 | 98.8 | −0.3 | 98.2 | 0.3 |
| III | 98.5 | 98.6 | −0.1 | 98.1 | 0.5 |
| IV | 98.5 | 98.5 | 0.0 | 97.8 | 0.7 |
| V | 98.4 | 98.0 | 0.4 | 97.3 | 1.1 |
| VI | 98.3 | 97.6 | 0.8 | 96.5 | 1.8 |

Table 6 shows that there is a correlation between pH increase and decrease in percent main peak, with the exception of the lowest pH (Formulation I). As the pH decreases, the stability of aflibercept, as determined by the reduced aggregation levels, increases.

Example 3

Aflibercept Stability of Formulations without a Buffering Agent with or without a Tonicity Agent and/or Surfactant Example 2 demonstrated aflibercept is stable, as determined by aggregation levels, in formulations without a buffering agent. The effect of salt and surfactant on the stability of aflibercept in formulations without a buffering agent at pH 6.2 was tested and compared to a formulation that contains a buffering agent at pH of 6.2.

To test the stability of aflibercept and the ability of the formulation to reach and maintain a target pH in a formulation without the presence of a buffering agent, aflibercept was purified from a cell culture using CEX column into a 100 mM Na acetate, 300 mM NaCl, pH 5.0 at 6.5 mg/mL. The pH of the composition was adjusted to pH 6.4 in order to achieve the final target pH of 6.2, accounting for the pH drift between the pH prior to the buffer exchange and post the buffer exchange that was observed in Example 2. The protein was then concentrated to 40 mg/mL and buffer exchanged with the formulations shown in Table 7. Surfactant was added to the different formulations post the buffer exchange. The pH and protein concentration post buffer exchange were tested and the samples were stored at the stress condition of 40° C. for up to two weeks. Eylea® is formulated as 40 mg/mL aflibercept in 10 mM sodium phosphate, 40 mM sodium chloride, 5% sucrose, 0.03% polysorbate 20 at a pH of 6.2, and this formulation, with a buffering agent, was included for comparison (Formulation A).

TABLE 7

Formulations A-F.

| Formulation | VEGF (mg/mL) | Buffering Agent | Tonicity Agent | Stabilizer | Surfactant | pH |
|---|---|---|---|---|---|---|
| A | 40 | 10 mM Sodium phosphate | 40 mM NaCl | 5% Sucrose | 0.03% PS20 | 6.2 |
| B | 40 | | | 5% Sucrose + 5% trehalose | 0.01% PS80 | 6.2 |
| C | 40 | | 5 mM NaCl | 5% Sucrose + 5% trehalose | 0.01% PS80 | 6.2 |
| D | 40 | | 10 mM NaCl | 5% Sucrose + 5% trehalose | 0.01% PS80 | 6.2 |
| E | 40 | | 20 mM NaCl | 5% Sucrose + 5% trehalose | 0.01% PS80 | 6.2 |
| F | 40 | | | 5% Sucrose + 5% trehalose | | 6.2 |

The pH for each formulation in Table 7 at T=0, at 1 week and at 2 weeks is shown in Table 8.

TABLE 8 pH Values Post Buffer Exchange and Storage at 40° C. for Formulations A-F.

| Formulation | pH at T = 0 | pH at T = 1 week | Delta from T = 0 | pH at T = 2 weeks | Delta from T = 0 |
|---|---|---|---|---|---|
| A | 6.4 | 6.4 | 0.0 | 6.5 | 0.1 |

TABLE 8-continued pH Values Post Buffer Exchange and Storage at 40° C. for Formulations A-F.

| Formulation | pH at T = 0 | pH at T = 1 week | Delta from T = 0 | pH at T = 2 weeks | Delta from T = 0 |
|---|---|---|---|---|---|
| B | 6.3 | 6.3 | 0.1 | 6.4 | 0.1 |
| C | 6.2 | 6.2 | 0.0 | 6.3 | 0.1 |
| D | 6.2 | 6.2 | 0.0 | 6.3 | 0.1 |
| E | 6.2 | 6.3 | 0.1 | 6.4 | 0.2 |
| F | 6.3 | 6.3 | 0.1 | 6.5 | 0.2 |

The starting material for the formulations in Table 7 was adjusted to pH 6.4 to accommodate the pH shift of the formulations post the buffer exchange, the pH of Formulation A at T=0 was 6.4 (Table 8), higher than the target pH of 6.2 (Table 7), but within the manufacturing variability of ±0.3 units. The difference between T=0 and following two weeks of storage at 40° C. was a maximum 0.2 pH units, a pH shift that is within typical manufacturing variability (usually ±0.3 pH units) and is not expected to impact the quality attributes of aflibercept. Moreover, the presence of a buffering agent resulted in a difference of 0.1 pH units, as with the formulations without a buffering agent. Thus, the pH remained stable over storage at stress conditions for all tested formulations.

To determine the stability of the formulations described in Table 7, the formulations were tested by SEC-UHPLC, as described in Example 1. The higher the main peak value (e.g., percentage) determined by SEC-UHPLC for a formulation, the more stable the formulation as it indicates a lower level of aggregation. Another indication of increased stability is a lack of change in the main peak value between an initial timepoint and a later timepoint as compared to another formulation.

The percentage of the main peak for each formulation in Table 7 was determined at timepoints 0, 1 week, and 2 weeks (T=0, T=1 w, T=2 w, respectively) for the formulations stored at 40° C., as shown in Table 9. The difference or delta value between the main peak percentages of T=0 and T=1 week and between the main peak percentages of T=0 and T=2 weeks for the formulations is also shown in Table 9.

TABLE 9

SEC-UHPLC Main Peak Results for Formulations A-F.

| Formulation | T = 0 | T = 1 week | Delta from T = 0 | T = 2 weeks | Delta from T = 0 |
|---|---|---|---|---|---|
| A | 97.9 | 94.5 | 3.4 | 92.5 | 5.4 |
| B | 98.0 | 96.4 | 1.6 | 95.5 | 2.5 |
| C | 98.0 | 96.3 | 1.7 | 95.3 | 2.7 |
| D | 98.0 | 96.1 | 1.9 | 94.9 | 3.1 |
| E | 98.0 | 95.8 | 2.2 | 94.4 | 3.6 |
| F | 98.0 | 96.6 | 1.4 | 95.7 | 2.3 |

Table 9 shows that all formulations without a buffering agent, regardless of salt or surfactant presence exhibited a higher main peak percentage, demonstrating reduced aggregation or increased stability, in comparison to the formulation containing the buffering agent (Formulation A). When comparing the aggregation levels between Formulation B and F, with and without surfactant, respectively, a comparable percent main peak is observed, demonstrating that aflibercept formulations without a buffering agent are stable with and without surfactant in terms of their aggregation as determined by SE-UHPLC.

Figure 3:
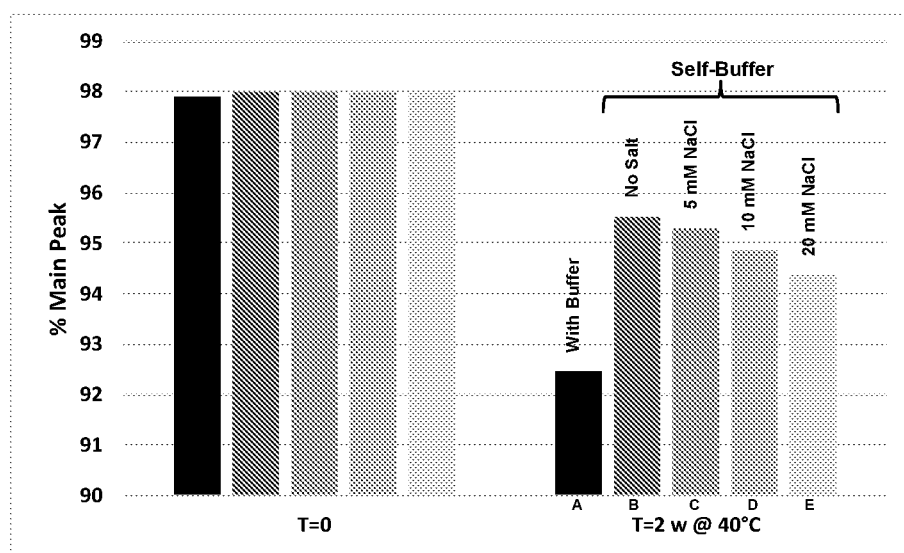
FIG. 3 shows the correlation between salt concentration and SEC-UHPLC percent main peak as described in Example 3.

A direct correlation is observed between the salt concentration and a decrease in the percent main peak, as can be seen in FIG. 3. However, all formulations without a buffering agent had lower aggregation levels in comparison to the buffered formulation (Formulation A).

Example 4

Aflibercept Stability of Formulations without a Buffering Agent for Three Larger Scale Studies Examples 1-3 were small-scale studies; ~2-10 mL undergoing buffer exchange and ~80 μL to ~280 μL placed on stability. Some of the formulations tested in the prior examples were examined at a larger-scale in three separate studies to demonstrate the applicability of the results to a larger-scale (Table 10). Eylea® is formulated as 40 mg/mL aflibercept in 10 mM sodium phosphate, 40 mM sodium chloride, 5% sucrose, 0.03% polysorbate 20 at a pH of 6.2, and this formulation, with a buffering agent and at a pH within the buffering range of the buffering agent, was included for comparison for all three studies (Formulations a, f, and j). Buffer exchange was conducted on 100 mL to 1000 mL and surfactant was added to the different formulations post the buffer exchange. The pH, osmolality, and protein concentration post buffer exchange were tested to ensure appropriate buffer exchange performance. The different formulations underwent a variety of process stresses including freeze-thaw, mixing, filtration, hold, filling, photoexposure, and transportation simulation (including vibration, pressure and drop-shock stresses). Following the process stresses samples from all formulations were placed on stability at varying storage temperatures of: 40° C., 30° C., 25° C., 5° C., and −30° C.

TABLE 10

Formulations a-k

| Study | Formulation | VEGF (mg/mL) | Buffering Agent | Tonicity Agent | Stabilizer | Surfactant | pH |
|---|---|---|---|---|---|---|---|
| 1 | a | 40 | 10 mM Sodium | 40 mM NaCl | 5% sucrose | 0.03% PS20 | 6.2 |

TABLE 10-continued

Formulations a-k

| Study | Formulation | VEGF (mg/mL) | Buffering Agent | Tonicity Agent | Stabilizer | Surfactant | pH |
|---|---|---|---|---|---|---|---|
|  | b | 40 | phosphate |  | 5% Sucrose + 3.5% trehalose dihydrate | 0.01% PS80 | 6.2 |
|  | c | 40 |  | 5 mM NaCl | 5% Sucrose + 3% trehalose dihydrate | 0.01% PS80 | 6.2 |
|  | d | 40 | 2.5 mM acetate |  | 5% trehalose 3.5% trehalose dihydrate | 0.01% PS80 | 6.2 |
|  | e | 40 | 2.5 mM acetate | 5 mM NaCl | 5% sucrose + 3% trehalose dihydrate | 0.01% PS80 | 6.2 |
| 2 | f | 40 | 10 mM Sodium phosphate | 40 mM NaCl | 5% sucrose | 0.03% PS20 | 6.2 |
|  | g | 40 |  |  | 5% sucrose + 3.5% trehalose dihydrate | 0.01% PS80 | 6.2 |
|  | h | 40 |  |  | 5% sucrose + 3.5% trehalose dihydrate | 0.02% PS80 | 6.2 |
|  | i | 40 |  |  | 5% sucrose + 3.5% trehalose dihydrate | 0.03% PS20 | 6.2 |
| 3 | j | 40 | 10 mM Sodium phosphate | 40 mM NaCl | 5% Sucrose | 0.03% PS20 | 6.2 |
|  | k | 40 |  |  | 5% Sucrose + 3.5% trehalose dihydrate | 0.01% PS80 | 6.2 |

The pH at T=0 and at various time points and various temperatures is presented in Tables 11A and B. The maximum and minimum pH of all the conditions tested in Tables 11A and B, as well as the highest difference between T=0 and the various conditions for all formulations is shown in Table 11C.

TABLE 11A pH Post Buffer Exchange and Storage at T = 0 and at 40° C. and 20° C. or 30° C. at Various Timepoints for Formulations a-k

| | | | 40° C. | | | 25° C. or 30° C.[2] | | | |
|---|---|---|---|---|---|---|---|---|---|
| Formulation | T = 0 | T = 1 w | T = 2 w | T = 4 w | T = 6 w or 12 w[1] | T = 2 w | T = 4 w | T = 12 w | T = 24 w |
| a | 6.3 | 6.3 | 6.3 | 6.3 | NT | 6.3 | 6.3 | 6.3 | NT |
| b | 6.3 | 6.3 | 6.2 | 6.2 | 6.4 | 6.4 | 6.3 | 6.1 | 6.3 |
| c | 6.2 | 6.3 | 6.2 | 6.3 | 6.4 | 6.3 | 6.3 | 6.1 | 6.1 |
| d | 6.2 | 6.3 | 6.3 | 6.3 | 6.4 | 6.3 | 6.4 | 6.1 | 6.2 |
| e | 6.2 | 6.3 | 6.2 | 6.3 | 6.3 | 6.3 | 6.4 | 6.1 | 6.1 |
| f | 6.3 | 6.2 | 6.2 | 6.2 | 6.2 | 6.2 | 6.2 | 6.2 | 6.1 |
| g | 6.3 | 6.4 | 6.3 | 6.3 | 6.2 | 6.2 | 6.3 | 6.2 | 6.2 |
| h | 6.3 | 6.3 | 6.3 | 6.2 | 6.2 | 6.2 | 6.3 | 6.2 | 6.2 |
| i | 6.3 | 6.3 | 6.2 | 6.2 | 6.2 | 6.1 | 6.3 | 6.2 | 6.2 |
| l | 6.2 | 6.1 | 6.1 | 6.1 | NT | 6.1 | 6.1 | 6.1 | 6.1 |
| k | 6.3 | 6.1 | 6.1 | 6.1 | NT | 6.1 | 6.1 | 6.1 | 6.1 |

[1]Storage condition was 6 weeks for Study 1, 12 weeks for Study 2 and was not tested for Study 3
[2]Storage condition was 25° C. for Study 1 and Study 3, and 30° C. for Study 2
NT = not tested

TABLE 11B pH Post Buffer Exchange and Storage of Formulations a-k at at 5° C. or −30° C. at Various Timepoints

| | 5° C. | | | −30° C. | |
|---|---|---|---|---|---|
| Formulation | T = 4 w | T = 12 w | T = 24 w | T = 12 w | T = 24 w |
| a | 6.3 | 6.1 | 6.2 | 6.3 | NT |
| b | 6.3 | 6.1 | 6.2 | 6.1 | 6.2 |
| c | 6.3 | 6.1 | 6.2 | 6.2 | 6.2 |
| d | 6.4 | 6.1 | 6.2 | 6.1 | 6.2 |
| e | 6.3 | 6.1 | 6.2 | 6.1 | 6.2 |
| f | 6.3 | 6.2 | 6.1 | 6.2 | 6.2 |
| g | 6.4 | 6.3 | 6.3 | 6.3 | 6.3 |
| h | 6.3 | 6.2 | 6.2 | 6.2 | 6.3 |
| i | 6.3 | 6.3 | 6.3 | 6.2 | 6.3 |
| j | 6.1 | 6.1 | 6.1 | 6.1 | 6.1 |
| k | 6.1 | 6.1 | 6.1 | 6.1 | 6.1 |

TABLE 11C

Maximum and Minimum pH of the Formulations in the Conditions of Tables 11A and 11B, and the Highest Difference Between T = 0 and the Various Conditions of Tables 11A and 11B

| Formulation | Max | Min | Highest Δ from T = 0 |
|---|---|---|---|
| a | 6.5 | 6.1 | 0.2 |
| b | 6.4 | 6.1 | 0.2 |
| c | 6.4 | 6.1 | 0.2 |
| d | 6.4 | 6.1 | 0.2 |
| e | 6.4 | 6.1 | 0.2 |
| f | 6.3 | 6.1 | 0.2 |
| g | 6.4 | 6.2 | 0.1 |
| h | 6.3 | 6.2 | 0.1 |
| i | 6.3 | 6.1 | 0.2 |
| j | 6.2 | 6.1 | 0.1 |
| k | 6.3 | 6.1 | 0.2 |

Table 11C shows that the highest difference between T=0 and the various conditions for all formulations regardless of the presence of a buffering agent is 0.2 pH units for up to 6 months of long-term storage. This demonstrates the capability of the formulations without a buffering agent to maintain a stable pH over long-term storage under various temperature storage conditions.

To determine the stability of the formulations described in Table 10, the formulations were tested by SEC-UHPLC, as described in Example 1. The higher the main peak value (e.g., percentage) determined by SEC-UHPLC for a formulation, the more stable the formulation, as it indicates a lower level of aggregation. Another indication of increased stability is a lack of change in the main peak value between an initial timepoint and a later timepoint as compared to another formulation. The results are presented in Tables 12A and B, as well as FIG. 4.

TABLE 12A

SEC-UHPLC Main Peak Results for Formulations a-k at T = 0 and at 40° C. and 20° C. or 30° C. at Various Timepoints

| | | 40° C. | | | | 25° C. or 30° C.[1] | | | |
|---|---|---|---|---|---|---|---|---|---|
| Formulation | T = 0 | T = 1 w | T = 2 w | T = 4 w | T = 12 w | T = 2 w | T = 4 w | T = 12 w | T = 24 w |
| a | 97.3 | 94.9 | 92.1 | 87.5 | NT | 97.1 | 96.9 | 96.6 | 96.4 |
| b | 98.1 | 97.2 | 96.1 | 94.1 | NT | 97.9 | 97.7 | 97.5 | 97.0 |
| c | 98.0 | 96.8 | 95.5 | 93.3 | NT | 97.7 | 97.6 | 97.3 | 96.6 |
| d | 98.1 | 97.2 | 96.2 | 94.5 | NT | 97.8 | 97.7 | 97.5 | 97.1 |
| e | 97.9 | 96.9 | 95.7 | 93.6 | NT | 97.8 | 97.6 | 97.4 | 96.9 |
| f | 98.2 | 96.7 | 95.4 | 92.4 | 79.9 | 97.9 | 97.5 | 96.5 | 95.3 |
| g | 97.9 | 97.4 | 96.7 | 95.0 | 87.7 | 97.8 | 97.5 | 96.6 | 95.9 |
| h | 97.9 | 97.4 | 96.6 | 95.0 | 87.5 | 97.8 | 97.6 | 96.6 | 95.7 |
| i | 97.9 | 97.4 | 96.6 | 95.0 | 87.4 | 97.8 | 97.5 | 96.7 | 96.1 |
| t | 98.6 | 97.2 | 95.6 | 92.7 | NT | 98.5 | 98.3 | 98.0 | 97.8 |
| k | 98.5 | 97.7 | 96.7 | 95.0 | NT | 98.4 | 98.2 | 97.8 | 97.7 |

[1]Storage condition was 25° C. for Study 1 and Study 3, and 30° C. for Study 2
NT = not tested

TABLE 12B

SEC-UHPLC Main Peak Results for Formulations a-k at 5° C. and −30° C. at Various Timepoints

| | 5° C. | | | −30° C. | |
|---|---|---|---|---|---|
| Formulation | T = 4 w | T = 12 w | T = 24 w | T = 12 w | T = 24 w |
| a | 97.2 | 97.3 | 97.7 | 97.4 | 98.0 |
| b | 98.0 | 98.0 | 98.0 | 98.1 | 98.1 |
| c | 97.8 | 97.8 | 97.8 | 97.9 | 98.0 |
| d | 97.8 | 98.0 | 97.9 | 98.0 | 98.0 |
| e | 97.8 | 97.9 | 97.8 | 97.9 | 97.9 |
| f | 98.2 | 98.1 | 98.1 | 98.2 | 98.2 |
| g | 98.0 | 97.9 | 97.9 | 98.0 | 98.1 |
| h | 97.9 | 98.0 | 98.0 | 98.0 | 98.1 |
| i | 98.0 | 97.9 | 97.9 | 97.9 | 98.1 |
| j | 98.5 | 98.4 | 98.5 | 98.5 | 98.7 |
| k | 98.5 | 98.3 | 98.3 | 98.4 | 98.6 |

As shown in Tables 12A and B, for all three studies (Formulations a-e, f-i, and j-k, for studies 1, 2, and 3, respectively), the formulations without a buffer (including formulations with a buffer but at a pH outside the buffering capacity of the buffer) in each study presented reduced or comparable aggregation as compared to the Eylea® formulation (Formulations a, f, and j, respectively), under all stability conditions tested.

In addition, the subvisible particle levels of the formulations were tested by light obscuration (HIAC) to examine the impact of the formulation on the protein's tendency to create particles. The results for the number of 2 μm, 5 μm 10 μm, 25 μm and 50 μm particles per mL for Formulations a-k are shown in Tables 13A-E, respectively.

TABLE 13A

Subvisible Particle Counts - 2 μm

| Form. | T = 0 | 25° C. or 30° C.[1] | | | | 5° C. | | | −30° C. | |
|---|---|---|---|---|---|---|---|---|---|---|
| | | T = 2 weeks | T = 4 weeks | T = 12 weeks | T = 24 weeks | T = 4 weeks | T = 12 weeks | T = 24 weeks | T = 12 weeks | T = 24 weeks |
| a | 620 | 477 | 649 | 374 | 164 | 155 | 317 | 1069 | 907 | 1395 |
| b | 2140 | 4267 | 1540 | 3954 | 3340 | 2690 | 3635 | 1879 | 3254 | 2779 |
| c | 3610 | 4912 | 702 | 4830 | 3930 | 4249 | 6157 | 3792 | 3440 | 2640 |
| d | 1797 | 3425 | 442 | 3772 | 2885 | 1799 | 3037 | 2027 | 2187 | 2077 |
| e | 2515 | 4259 | 540 | 5142 | 3537 | 2860 | 4052 | 2712 | 2819 | 1652 |
| f | 2674 | 6382 | 3047 | 5855 | 2040 | 2877 | 3139 | 1539 | 4180 | 3274 |
| g | 1760 | 5417 | 2874 | 6212 | 3859 | 2984 | 3089 | 3275 | 4560 | 2730 |
| h | 2800 | 9580 | 5060 | 10397 | 6017 | 3885 | 6400 | 4332 | 6077 | 3599 |
| i | 3142 | 9120 | 4530 | 10349 | 8404 | 6100 | 7865 | 5499 | 4762 | 3702 |
| l | 220 | 240 | 99 | 80 | NT | 279 | 234 | NT | 557 | NT |
| k | 4272 | 3357 | 3014 | 2750 | NT | 4320 | 3100 | NT | 2619 | NT |

[1] Storage condition was 25° C. for Study 1 and Study 3, and 30° C. for Study 2
NT = not tested

TABLE 13B

Subvisible Particle Counts - 5 μm

| Form. | T = 0 | 25° C. or 30° C.[1] | | | | 5° C. | | | −30° C. | |
|---|---|---|---|---|---|---|---|---|---|---|
| | | T = 2 weeks | T = 4 weeks | T = 12 weeks | T = 24 weeks | T = 4 weeks | T = 12 weeks | T = 24 weeks | T = 12 weeks | T = 24 weeks |
| a | 40 | 52 | 29 | 37 | 15 | 14 | 25 | 95 | 70 | 134 |
| b | 90 | 497 | 125 | 484 | 285 | 269 | 300 | 199 | 262 | 327 |
| c | 284 | 847 | 125 | 747 | 585 | 517 | 775 | 489 | 322 | 309 |
| d | 130 | 359 | 44 | 399 | 280 | 199 | 327 | 257 | 160 | 202 |
| e | 202 | 440 | 64 | 580 | 362 | 370 | 402 | 305 | 207 | 159 |
| f | 150 | 594 | 127 | 434 | 114 | 210 | 225 | 70 | 297 | 257 |
| g | 134 | 515 | 199 | 747 | 407 | 235 | 372 | 310 | 390 | 132 |
| h | 437 | 1282 | 400 | 1537 | 849 | 339 | 702 | 360 | 617 | 287 |
| l | 409 | 1105 | 365 | 1380 | 1470 | 512 | 804 | 399 | 499 | 272 |
| j | 29 | 30 | 7 | 15 | NT | 12 | 25 | NT | 44 | NT |
| k | 420 | 277 | 184 | 199 | NT | 377 | 232 | NT | 195 | NT |

[1] Storage condition was 25° C. for Study 1 and Study 3, and 30° C. for Study 2
NT = not tested

TABLE 13C

Subvisible Particle Counts - 10 μm

| Form. | T = 0 | 25° C. or 30° C.[1] | | | | 5° C. | | | −30° C. | |
|---|---|---|---|---|---|---|---|---|---|---|
| | | T = 2 weeks | T = 4 weeks | T = 12 weeks | T = 24 weeks | T = 4 weeks | T = 12 weeks | T = 24 weeks | T = 12 weeks | T = 24 weeks |
| a | 4 | 5 | 4 | 5 | 4 | 4 | 9 | 5 | 5 | 9 |

TABLE 13C-continued

Subvisible Particle Counts - 10 μm

| | | 25° C. or 30° C.[1] | | | | 5° C. | | | −30° C. | |
|---|---|---|---|---|---|---|---|---|---|---|
| Form. | T = 0 | T = 2 weeks | T = 4 weeks | T = 12 weeks | T = 24 weeks | T = 4 weeks | T = 12 weeks | T = 24 weeks | T = 12 weeks | T = 24 weeks |
| b | 7 | 34 | 14 | 32 | 9 | 19 | 20 | 5 | 19 | 20 |
| c | 19 | 72 | 19 | 57 | 82 | 17 | 72 | 25 | 19 | 9 |
| d | 10 | 20 | 2 | 20 | 20 | 7 | 34 | 12 | 24 | 9 |
| e | 25 | 12 | 10 | 34 | 37 | 12 | 24 | 12 | 9 | 2 |
| f | 10 | 15 | 9 | 17 | 10 | 15 | 14 | 5 | 5 | 7 |
| g | 12 | 12 | 12 | 32 | 15 | 12 | 15 | 24 | 19 | 7 |
| h | 69 | 50 | 10 | 67 | 49 | 12 | 20 | 30 | 17 | 27 |
| i | 22 | 47 | 22 | 87 | 94 | 15 | 29 | 29 | 5 | 22 |
| j | 2 | 2 | 0 | 2 | NT | 2 | 4 | NT | 14 | NT |
| k | 14 | 5 | 0 | 14 | NT | 9 | 12 | NT | 9 | NT |

[1]Storage condition was 25° C. for Study 1 and Study 3, and 30° C. for Study 2
NT = not tested

TABLE 13D

Subvisible Particle Counts - 25 μm

| | | 25° C. or 30° C.[1] | | | | 5° C. | | | −30° C. | |
|---|---|---|---|---|---|---|---|---|---|---|
| Form. | T = 0 | T = 2 weeks | T = 4 weeks | T = 12 weeks | T = 24 weeks | T = 4 weeks | T = 12 weeks | T = 24 weeks | T = 12 weeks | T = 24 weeks |
| a | 0 | 2 | 0 | 0 | 0 | 0 | 0 | 0 | 4 | 0 |
| b | 0 | 0 | 0 | 2 | 0 | 2 | 2 | 0 | 2 | 2 |
| c | 0 | 0 | 0 | 0 | 0 | 0 | 5 | 2 | 0 | 0 |
| d | 0 | 2 | 0 | 0 | 0 | 0 | 7 | 0 | 5 | 2 |
| e | 0 | 0 | 0 | 2 | 2 | 0 | 0 | 2 | 0 | 0 |
| f | 2 | 0 | 0 | 0 | 0 | 0 | 2 | 0 | 2 | 0 |
| g | 2 | 0 | 0 | 0 | 2 | 0 | 4 | 0 | 2 | 2 |
| h | 0 | 0 | 0 | 2 | 2 | 0 | 2 | 2 | 0 | 2 |
| i | 4 | 4 | 0 | 0 | 5 | 0 | 0 | 0 | 2 | 4 |
| j | 0 | 0 | 0 | 0 | NT | 0 | 0 | NT | 0 | NT |
| k | 0 | 2 | 0 | 0 | NT | 0 | 0 | NT | 0 | NT |

[1]Storage condition was 25° C. for Study 1 and Study 3, and 30° C. for Study 2
NT = not tested

TABLE 13E

Subvisible Particle Counts - 50 μm

| | | 25° C. or 30° C.[1] | | | | 5° C. | | | −30° C. | |
|---|---|---|---|---|---|---|---|---|---|---|
| Form. | T = 0 | T = 2 weeks | T = 4 weeks | T = 12 weeks | T = 24 weeks | T = 4 weeks | T = 12 weeks | T = 24 weeks | T = 12 weeks | T = 24 weeks |
| a | 0 | 0 | 0 | 0 | 0 | 0 | 0 | 0 | 0 | 0 |
| b | 0 | 0 | 0 | 0 | 0 | 0 | 0 | 0 | 0 | 0 |
| c | 0 | 0 | 0 | 0 | 0 | 0 | 2 | 0 | 0 | 0 |
| d | 0 | 0 | 0 | 0 | 0 | 0 | 0 | 0 | 0 | 2 |
| e | 0 | 0 | 0 | 2 | 0 | 0 | 0 | 0 | 0 | 0 |
| f | 0 | 0 | 0 | 0 | 0 | 0 | 0 | 0 | 0 | 0 |
| g | 0 | 0 | 0 | 0 | 0 | 0 | 0 | 0 | 0 | 0 |
| h | 0 | 0 | 0 | 0 | 0 | 0 | 0 | 0 | 0 | 0 |
| i | 0 | 0 | 0 | 0 | 0 | 0 | 0 | 0 | 0 | 0 |
| j | 0 | 0 | 0 | 0 | NT | 0 | 0 | NT | 0 | NT |
| k | 0 | 0 | 0 | 0 | NT | 0 | 0 | NT | 0 | NT |

[1]Storage condition was 25° C. for Study 1 and Study 3, and 30° C. for Study 2
NT = not tested The formulations without a buffer (including formulations with a buffer but having a pH outside the buffering capacity of the buffer) exhibited subvisible counts that were not significantly different than that of the formulations comprising a buffer and having a pH within the buffering capacity of the buffer (i.e., Formulations a, f, and j).

While the present invention has been described in terms of various embodiments, it is understood that variations and modifications will occur to those skilled in the art. Therefore, it is intended that the appended claims cover all such equivalent variations that come within the scope of the invention as claimed. In addition, the section headings used herein are for organizational purposes only and are not to be construed as limiting the subject matter described.

All references cited in this application are expressly incorporated by reference herein for any purpose.

What is claimed is:

1. A formulation comprising: (a) aflibercept; (b) 5% (w/v) sucrose; and (c) trehalose; wherein the formulation does not comprise a buffer; wherein the pH is between 5.0 and 6.8; wherein the pH remains within 0.3 pH units of the starting pH after two weeks of storage at 40° C.; and wherein the formulation is formulated for intravitreal administration.

2. The formulation of claim 1, wherein the pH is about 5.2, about 5.5, about 5.8, about 6.0, about 6.2, about 6.3, about 6.4, or about 6.5.

3. The formulation of claim 1, wherein the concentration of aflibercept is about 40 mg/ml.

4. The formulation of claim 1, wherein the concentration of trehalose is between 2% and 10% (w/v).

5. The formulation of claim 1, wherein the concentration of trehalose about 3.5%, or about 5% (w/v).

6. The formulation of claim 1, wherein the total concentration of sucrose and trehalose is about 8.5%, or about 10% (w/v).

7. The formulation of claim 1, further comprising a surfactant.

8. The formulation of claim 7, wherein the surfactant is polysorbate 20, polysorbate 80 or poloxamer 188.

9. The formulation of claim 7, wherein the concentration of the surfactant is between 0.001 and 0.1%.

10. The formulation of claim 1, further comprising a tonicity agent.

11. The formulation of claim 10, wherein the tonicity agent is sodium chloride or potassium chloride.

12. The formulation of claim 11, wherein the concentration of the tonicity agent is between 1 mM and 150 mM.

* * * * *